United States Patent
Wu et al.

(10) Patent No.: US 10,786,674 B2
(45) Date of Patent: Sep. 29, 2020

(54) MEDICAL THERAPY TARGET DEFINITION

(71) Applicant: Medtronic, Inc., Minneapolis, MN (US)

(72) Inventors: Jianping Wu, Shoreview, MN (US); Dwight E. Nelson, Shoreview, MN (US); Gabriela C. Molnar, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 639 days.

(21) Appl. No.: 15/064,337

(22) Filed: Mar. 8, 2016

(65) Prior Publication Data

US 2017/0259064 A1   Sep. 14, 2017

(51) Int. Cl.
    *A61N 1/36*     (2006.01)
    *A61N 1/05*     (2006.01)
    *A61B 5/00*     (2006.01)

(52) U.S. Cl.
    CPC ........ *A61N 1/36139* (2013.01); *A61B 5/4076* (2013.01); *A61N 1/0534* (2013.01);
    (Continued)

(58) Field of Classification Search
CPC ............ A61N 1/36135; A61N 1/36139; A61N 1/36082
See application file for complete search history.

(56) References Cited

U.S. PATENT DOCUMENTS 6,647,296 B2  11/2003  Fischell et al.
6,993,384 B2   1/2006  Bradley et al.
(Continued)

FOREIGN PATENT DOCUMENTS

EP      1191972 B1 *  8/2005  ............... A61B 5/11
WO      2007138598 A2  12/2007
(Continued)

OTHER PUBLICATIONS

Buhlmann et al., "Modeling of a Segmented Electrode for Desynchronizing Deep Brain Stimulation," Frontiers in Neuroengineering, vol. 4, Article 15, retrieved from www.frontiersin.org, Dec. 2011, 8 pp.
(Continued)

*Primary Examiner* — Michael J D Abreu
(74) *Attorney, Agent, or Firm* — Shumaker & Sieffert, P.A.

(57) ABSTRACT

In some examples, a system may include a plurality of electrodes, electrical stimulation circuitry, and a controller. The controller may be configured to select one or more parameters of therapy to be delivered to a brain of a patient and to control the electrical stimulation circuitry to deliver the therapy to the brain of the patient based on the selected parameters and via a first one or more electrodes of the plurality of electrodes. The parameters may be defined based on a first plurality of electrical signals sensed at a plurality of different positions within the brain of the patient when electrical stimulation is not delivered at each of the positions and a second plurality of electrical signals sensed at each of the plurality of different positions within the brain of the patient in response to electrical stimulation delivered at each of the positions at a plurality of different intensities.

42 Claims, 10 Drawing Sheets

(52) U.S. Cl.
CPC ..... *A61N 1/36067* (2013.01); *A61N 1/36185* (2013.01); *A61B 5/4082* (2013.01)

(56) References Cited

U.S. PATENT DOCUMENTS

| | | | |
|---|---|---|---|
| 7,822,482 | B2 | 10/2010 | Gerber |
| 7,957,808 | B2 | 6/2011 | Dawant et al. |
| 7,983,757 | B2 | 7/2011 | Miyazawa et al. |
| 8,099,170 | B2 | 1/2012 | Jensen et al. |
| 8,280,514 | B2 | 10/2012 | Lozano et al. |
| 8,447,406 | B2 | 5/2013 | Wu et al. |
| 8,473,063 | B2 | 6/2013 | Gupta et al. |
| 8,532,757 | B2 | 9/2013 | Molnar et al. |
| 8,565,886 | B2 | 10/2013 | Nelson et al. |
| 8,583,254 | B2 | 11/2013 | Jensen et al. |
| 8,761,890 | B2 | 6/2014 | Gupta et al. |
| 8,868,173 | B2 | 10/2014 | Nelson et al. |
| 8,886,323 | B2 | 11/2014 | Wu et al. |
| 8,892,207 | B2 | 11/2014 | Nelson et al. |
| 8,914,119 | B2 | 12/2014 | Wu et al. |
| 8,918,176 | B2 | 12/2014 | Nelson et al. |
| 8,954,152 | B2 | 2/2015 | Gupta et al. |
| 2001/0051819 | A1 | 12/2001 | Fischell et al. |
| 2003/0149457 | A1* | 8/2003 | Tcheng ............... A61N 1/36067 607/48 |
| 2005/0075669 | A1* | 4/2005 | King ................ A61N 1/36021 607/2 |
| 2006/0017749 | A1 | 1/2006 | McIntyre et al. |
| 2007/0203538 | A1 | 8/2007 | Stone et al. |
| 2007/0203545 | A1 | 8/2007 | Stone et al. |
| 2007/0203546 | A1 | 8/2007 | Stone et al. |
| 2007/0225674 | A1 | 9/2007 | Molnar et al. |
| 2007/0288064 | A1 | 12/2007 | Butson et al. |
| 2008/0215125 | A1 | 9/2008 | Farah et al. |
| 2008/0269836 | A1 | 10/2008 | Foffani et al. |
| 2009/0099627 | A1 | 4/2009 | Molnar et al. |
| 2009/0118787 | A1 | 5/2009 | Moffitt et al. |
| 2009/0264954 | A1 | 10/2009 | Rise et al. |
| 2010/0036468 | A1 | 2/2010 | Decre et al. |
| 2010/0041972 | A1 | 2/2010 | Mason |
| 2010/0204748 | A1 | 8/2010 | Lozano et al. |
| 2010/0241020 | A1 | 9/2010 | Zaidel et al. |
| 2011/0047795 | A1 | 3/2011 | Turner et al. |
| 2011/0264165 | A1 | 10/2011 | Molnar et al. |
| 2012/0010552 | A1 | 1/2012 | Greer, Jr. et al. |
| 2012/0053658 | A1 | 3/2012 | Gabriela et al. |
| 2012/0101547 | A1 | 4/2012 | Jensen et al. |
| 2012/0101552 | A1 | 4/2012 | Lazarewicz et al. |
| 2012/0150256 | A1 | 6/2012 | Martens |
| 2012/0271375 | A1 | 10/2012 | Wu et al. |
| 2013/0030500 | A1 | 1/2013 | Toader et al. |
| 2013/0053722 | A1 | 2/2013 | Carlson et al. |
| 2013/0123600 | A1 | 5/2013 | Tcheng |
| 2013/0131770 | A1 | 5/2013 | Rezai |
| 2014/0107731 | A1 | 4/2014 | Stone et al. |
| 2015/0088228 | A1 | 3/2015 | Moffitt |

FOREIGN PATENT DOCUMENTS

| | | | | |
|---|---|---|---|---|
| WO | WO-2007138598 | A2 * | 12/2007 | ........... A61B 5/0478 |
| WO | 2012155183 | A1 | 11/2012 | |

OTHER PUBLICATIONS

Zaidel et al., "Subthalamic span of oscillations predicts deep brain stimulation efficacy for patients with Parkinson's Disease," Brain, A Journal of Neurology, vol. 133 Oxford University Press, May 3, 2010, 15 pp.

Eusebio et al., "Deep Brain Stimulation can suppress pathological synchronization in parkinsonian patients," Journal of Neurology, Neurosugery, and Psychiatry, BMJ Publishing Group, 2010, 82 (5), p. 569, 29 pp.

International Search Report and Written Opinion from International Application No. PCT/US2017/015827, dated Mar. 29, 2017, 9 pp.

* cited by examiner

MEDICAL THERAPY TARGET DEFINITION

TECHNICAL FIELD

The disclosure relates to defining a target for medical therapy.

BACKGROUND

Implantable medical devices, such as electrical stimulators, may be used in different therapeutic applications. In some therapy systems, an implantable electrical stimulator delivers electrical stimulation therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may include the configuration of electrodes and/or electrical stimulation intensities used to deliver the electrical stimulation therapy.

SUMMARY

In general, the disclosure is directed toward defining a therapy target, which may be a portion of the anatomy that is targeted to receive therapy, and delivering therapy based on the therapy target definition. In deep brain stimulation (DBS), for example, a therapy target definition may characterize a source of oscillation within a brain of a patient, such as a source of oscillations in a specific frequency range or band that may be associated with one or more diseases or disorders; for example, a source of oscillation in the beta frequency band may be associated with certain symptoms of Parkinson's disease.

In some examples, the therapy target definition may correspond to a spatial characteristic, such as size, shape, volume, origin and/or location of the oscillation signal source within the brain. In some examples, the therapy target definition may be used by a medical device system to define parameters for delivery of electrical stimulation to alleviate symptoms of the diseases or disorders associated with the source. In some examples, the parameters may be selected at least in part as a function of the therapy target definition, e.g., as a function of a spatial characteristic of the source or affected area represented by the therapy target definition.

In other examples, the therapy target definition may be used by a medical device system to define therapy for forming one or more lesions corresponding to the spatial extent of an oscillation signal source, to monitor changes, such as growth, in the spatial extent of the oscillation signal source, to monitor for movement of a lead or other medical component with respect to the oscillation signal source, or in any other suitable manner according to particular needs.

In some examples, defining the therapy target may comprise defining parameters for delivering therapy, including, for example, selecting electrodes for delivery of electrical stimulation and/or selecting intensities of electrical stimulation delivered by the selected electrodes. For example, selected electrodes and selected intensities may define the therapy target and directly form parameters for delivery of electrical stimulation. In other examples, the therapy target may be defined and then the stimulation parameters may be selected based on the therapy target definition.

The therapy target may be defined by sensing electrical signals at a plurality of positions within a brain, delivering electrical stimulation at the plurality of positions within the brain, sensing electrical signals in response to the delivered electrical signals at the plurality of positions, and defining the therapy target based on the electrical signals sensed before delivery of electrical stimulation and in response to the delivery of the electrical stimulation. Throughout this application, references to an oscillation signal source or source may be used to refer to an origin of oscillation within the brain and/or an affected area of the brain that is impacted by the origin and the systems and methods described may be used to define a spatial extent of the origin and/or the affected area.

Defining a therapy target that corresponds to a spatial extent of a source of beta oscillation or other physiological signals may provide for improved treatment of symptoms caused by or associated with oscillations emitted by the source. For example, information corresponding to the spatial extent of the source may be used to deliver appropriate electrical stimulation with appropriate parameters including, for example, position, amplitude, frequency, and/or pulse width, to form a lesion corresponding to the spatial extent of the source, perform plasticity inductions, perform drug infusions, more broadly map states and extents of brain dysfunction, monitor for changes in the spatial extent of the source, and/or monitor for movement of a lead with respect to the source. The described method of defining the therapy target may be performed, in some examples, using a single lead, reducing risks associated with multiple leads including, for example, increased risk of brain tissue damage or hemorrhage.

In one example, the disclosure is directed to a method for delivering therapy to a patient. The method may include selecting one or more parameters of therapy to be delivered to a brain of a patient. The parameters may be defined based on a first plurality of electrical signals sensed at each of a plurality of different positions within the brain of the patient when electrical stimulation is not delivered at each of the positions; and a second plurality of electrical signals sensed at each of at least a subset of the plurality of different positions within the brain of the patient in response to electrical stimulation delivered at each of the at least the subset of the positions at a plurality of different intensities. The method may include delivering the therapy to the brain of the patient based on the selected parameters.

In another example, the disclosure is directed to a system for delivering electrical stimulation. The system may include a plurality of electrodes, electrical stimulation circuitry, and a controller configured to select one or more parameters of therapy to be delivered to a brain of a patient. The parameters may be defined based on a first plurality of electrical signals, sensed at a plurality of different positions within the brain of the patient when electrical stimulation is not delivered at each of the positions, and a second plurality of electrical signals, sensed at each of at least a subset of the different positions within the brain of the patient in response to electrical stimulation delivered at each of the at least a subset of the different positions at a plurality of different intensities. The controller may be further configured to control the electrical stimulation circuitry to deliver the therapy to the brain of the patient based on the selected parameters and via a first one or more electrodes of the plurality of electrodes.

In yet another example, the disclosure is directed to a system for delivering electrical stimulation. The system may include means for selecting one or more parameters of therapy to be delivered to a brain of a patient. The parameters may be defined based on a first plurality of electrical signals, sensed at a plurality of different positions within the brain of the patient when electrical stimulation is not delivered at each of the positions, and a second plurality of electrical signals, sensed at each of at least a subset of the different positions within the brain of the patient in response to electrical stimulation delivered at each of the at least a subset of the different positions at a plurality of different intensities. The system may further include means for delivering the therapy to the brain of the patient and means for controlling the means for delivering therapy to deliver the therapy to the brain of the patient based on the selected parameters.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1A:
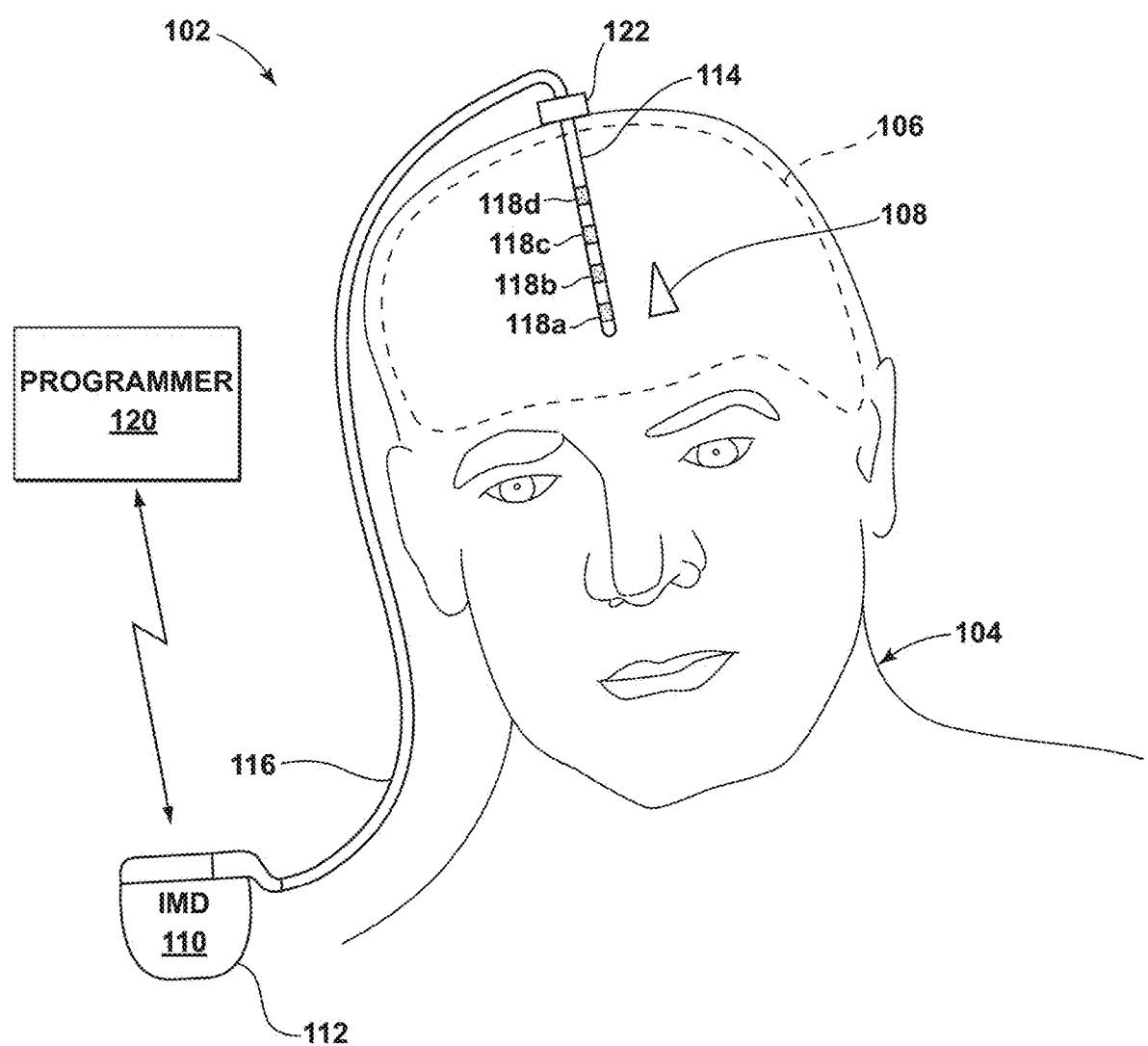
FIGS. 1A and 1B are conceptual diagrams illustrating an example deep brain stimulation (DBS) system.
Figure 1B:
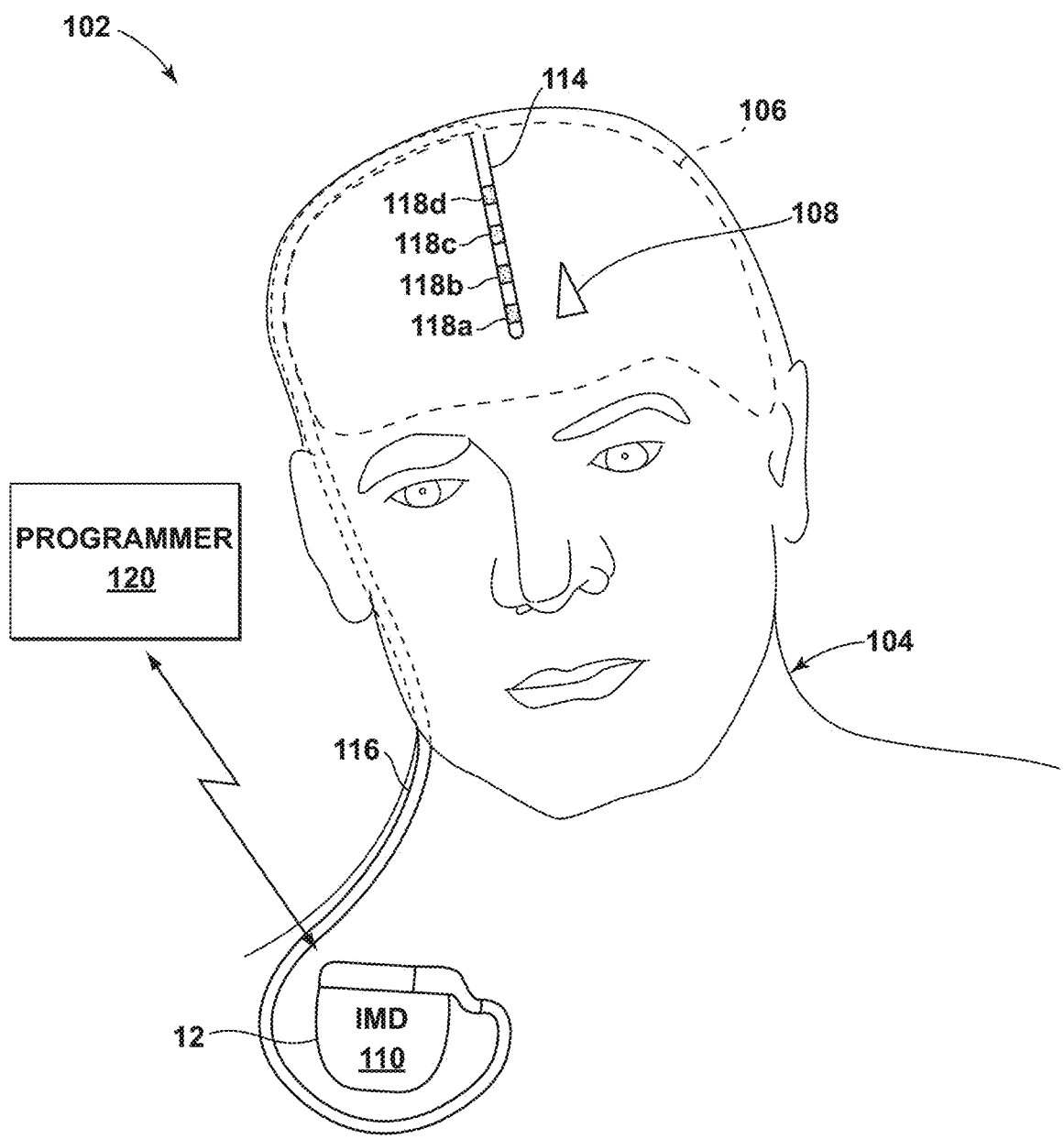

FIGS. 1A and 1B are conceptual diagrams illustrating an example deep brain stimulation (DBS) system 102. System 102 may deliver electrical stimulation therapy to tissue in the brain of a patient 104 to control a patient condition, such as a movement disorder, neurodegenerative impairment, a mood disorder or a seizure disorder of the patient 104. Patient 104 ordinarily will be a human patient. In some cases, however, therapy system 102 may be applied to other mammalian or non-mammalian, non-human patients. While movement disorders and neurodegenerative impairment are primarily referred to herein, in other examples, therapy system 102 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post traumatic stress disorder, sleep disorders, dysthymic disorder, Tourette's syndrome, addiction disorders, and obsessive-compulsive disorder (OCD)).

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions. Although movement disorders are primarily referred to throughout the remainder of the disclosure, the therapy systems and methods described herein are also useful for managing (e.g., controlling patient symptoms) other patient conditions, such as neurodegenerative impairment or mood disorders.

Beta oscillations or oscillations in other frequency ranges in the subthalamic nucleus ("STN") of Parkinson's Disease ("PD") patients may be a physiomarker or biomarker related to PD motor performance and may be related to PD and disease progression. Similar oscillatory activities in brain tissue may be related to other neurological dysfunctions. Different movement disorder symptoms may be detected based on biomarkers related to different frequency bands of a bioelectrical brain signal. An example of frequency bands is shown in Table 1 below:

TABLE 1

| Frequency (f) Band Hertz (Hz) | Frequency Information |
|---|---|
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

System 102 may select the frequency band to monitor based on the patient's symptoms. While for ease of reference, the following discussion describes examples of using beta activity as a biomarker of interest, it will be understood that one or more other frequency bands, or ratios between two frequency bands, may be used in addition to, or instead of, the beta band frequency according to examples of this disclosure.

The goal during DBS implantation and programming may be to set the lead position and stimulation parameters such that they maximally suppress beta or other oscillatory activity. Studies demonstrate beta oscillations may not come from a point source, but rather the source may extend for ranges from 0.5 mm to 3.5 mm along the DBS lead trajectory. See Zaidel A, Spivak A, Grieb B, Bergman H, Israel Z. Subthalamic span of beta oscillations predicts deep brain stimulation efficacy for patients with Parkinson's disease. Brain 133 (Pt 7): 2007-2021, 2010. PMID 20534648.). Further, the spatial extent of the beta activity may predict disease severity, disease progression or the clinical outcome using DBS therapy. A larger spatial extent of beta activity along the lead trajectory may be correlated with improved outcomes for DBS. For these reasons it may be desirable to quantify the spatial extent of beta oscillations in the brain and, for DBS therapy, deliver stimulation to cover the entire spatial extent of the beta oscillations. Similar mapping may be useful for other therapeutic approaches (such as lesions, plasticity inductions, drug infusions or more broadly mapping states and extents of brain dysfunction).

One potential problem for DBS is difficulty in determining the number and/or intensity of specific electrical contacts to deliver electrical stimulation for DBS therapy. Relying solely on sensing information may not allow determination of the spatial distribution of the source. For example, multiple "shapes" or patterns of source distributions may produce identical profile of recorded potentials at the electrode contacts, as discussed below with reference to FIGS. 4A and 4B. To solve this problem, a combination of both sensing and stimulation may be used to adequately map the distribution of the source. In this manner, the spatial extent or pattern of source distribution within the brain may be determined. And for DBS, effective stimulation can be delivered to the distributed source to be maximally effective as a therapy. With the spatial distribution mapped, appropriate stimulation contacts and stimulation parameters (intensity, frequency and pulse width) may be applied to provide effective therapy.

Current DBS practice permits the measurement of beta or other activity along the trajectory of the DBS lead by recording local field potentials or micro electrode recordings (MERs) while moving the lead towards the stimulation target or along the length of an implanted lead. However, this method may not allow sensing of the "width" or radial extent of the spatial signal at an angle perpendicular to the lead axis. One concept to solve this problem may be inserting multiple test leads/electrodes to "triangulate" the extent and boundaries of beta activity. But this method may carry the increased risk of brain tissue damage or hemorrhage caused by multiple lead tracks. The method described below relies only upon a single lead track, therefore reducing risk of multiple leads.

Therapy system 102 may include medical device programmer 120, implantable medical device (IMD) 110, lead extension 116, and lead 114 with electrodes 118a, 118b, 118c, and 118d. In the examples shown in FIGS. 1A and 1B, electrodes 118 of lead 114 may be positioned to deliver electrical stimulation to a tissue site within brain 106, such as a deep brain site under the dura mater of brain 106 of patient 104. Brain 106 may include a region of tissue that operates as a source of brain signal oscillations, such as beta band oscillations. In addition to temporal characteristics such as the frequency of oscillation, this source may be characterized by spatial characteristics, such as a position, spatial size and spatial shape. One example of such a source is represented in FIG. 1A with reference numeral 108. Source 108 may be a source of beta oscillations within brain 106, or a source of other oscillations in other therapy applications and may include an origin of the oscillation and/or an affected area of the brain. In some examples, source 108 may extend along the length of lead 114 in a range of approximately 0.5 mm to 3.5 mm.

In some examples, delivery of stimulation to one or more regions of brain 106, such as the subthalamic nucleus, globus pallidus or thalamus, may be an effective treatment to manage movement disorders, such as Parkinson's disease. Electrodes 118 may also be positioned to sense bioelectrical brain signals within brain 106 of patient 104. In some examples, some of electrodes 118a, 118b, 118c, and 118d may be configured to sense bioelectrical brain signals and others of electrodes 118a, 118b, 118c, and 118d may be configured to deliver electrical stimulation to brain 106. In other examples, all of electrodes 118a, 118b, 118c, and 118d may be configured to both sense bioelectrical brain signals and deliver electrical stimulation to brain 106, e.g., on a selective basis. Electrodes 118a, 118b, 118c, and 118d may include any suitable types of electrodes including, for example, ring electrodes, segmented electrodes, or pad electrodes. Each of electrodes 118a, 118b, 118c, and 118d may be used to refer to a single electrode, an electrode segment, or a group of electrodes or electrode segments corresponding to one or more axial and/or circumferential positions on lead 114.

IMD 110 may include an electrical stimulation circuitry 204 (FIG. 2) that generates and delivers electrical stimulation to patient 104 via one or more of electrodes 118a, 118b, 118c, and 118d of lead 114 and sensing circuitry 206 senses bioelectrical signals within brain 106 via one of more electrodes 118a, 118b, 118c, and 118d of lead 114. In some examples, the bioelectrical signals sensed within brain 106 may reflect changes in electrical current produced by the sum of electrical potential differences across brain tissue. Examples of bioelectrical brain signals include, but are not limited to, electrical signals generated from local field potentials (LFP) sensed within one or more regions of brain 106, such as an electroencephalogram (EEG) signal, or an electrocorticogram (ECoG) signal. Local field potentials, however, may include a broader genus of electrical signals within brain 106 of patient 104. LFP signals may have frequency content spanning one or more frequency ranges, including beta band signals, gamma band signals, and/or other signal ranges such as those discussed above that may provide information useful for defining a therapy target, which may be a portion of the anatomy that is targeted to receive therapy, corresponding to source 108. Various techniques may be used to extract the frequency ranges. For instance, band-pass filters may be used to extract selected frequency ranges from the time-domain LFP signal and the amplitude (e.g., in microvolts) or power level of the signal in the selected frequency range may be measured. For example, the relative beta band power may be determined as a ratio of the beta band power to a voltage amplitude of the signal. The voltage amplitude may be a mean or median voltage amplitude of the signal over a predetermined range of time, such as about ten seconds to about two minutes, although other time ranges are also contemplated. The voltage amplitudes of the bioelectrical brain signals may be calibration coefficients that help minimize variability between the power levels of the bioelectrical brain signals in a particular frequency band that is attributable to differences in the overall signal power level.

In some examples, transforms such as a fast Fourier transforms (FFTs) may be used to convert the LFP or other time-domain signal to the frequency domain so that the signal level in a particular frequency band may be determined. As one example, a power spectral density (PSD) may be determined in microvolts squared per Hertz ($\mu v^2/Hz$) for a particular frequency band based on the frequency domain data.

In some examples, microelectrode recording (MER) data of the type generated from acute use/mapping leads or microelectrodes provided on chronic leads may be used in additional to, or instead of, the LFP data. In other examples, microelectrodes may be used to record macro LFPs for use according to the disclosed techniques. Other data from other types of recording methodologies may be used. Thus, the current disclosure is not limited by any particular structure or technique used to record the sensed signals, and any technique suitable for recording the signals is contemplated.

In some examples, the bioelectrical brain signals may be sensed within the same region of brain 106 as a target tissue site for the electrical stimulation. As previously indicated, these tissue sites may include tissue sites within the thalamus, subthalamic nucleus or globus pallidus of brain 106, as well as other target tissue sites. The specific target tissue sites and/or regions within brain 106 may be selected based on the patient condition. Thus, in some examples, both a stimulation electrode combination and sense electrode combinations may be selected from the same set of electrodes 118a, 118b, 118c, and 118d. In other examples, the electrodes used for delivering electrical stimulation may be different than the electrodes used for sensing bioelectrical brain signals.

In some examples, the delivery of electrical stimulation and sensing of electrical signals may be used to define a therapy target and to deliver therapy based on the therapy target definition. In some examples, defining the therapy target may comprise defining parameters for delivering therapy, including selecting electrodes for delivery of electrical stimulation and/or selecting intensities of electrical stimulation, which may be a function of amplitude, pulse width, and pulse rate. In such an example, sensed signals and intensities selected to define the parameters may be representative of a therapy target that is a function of a spatial extent of an oscillatory source, and also serve as parameters for delivery of electrical stimulation therapy. In other examples, the therapy target may be defined and then the parameters may be selected based on the therapy target definition. Source 108, for example, may be a source that exhibits a detectable signal characteristic, such as beta oscillations and IMD 110 may be used to define a therapy target corresponding to a spatial extent of source 108 and to deliver therapy based on the therapy target definition. Movement disorders may be promoted by beta band oscillations emitted by tissue associated with a source, such as source 108. As will be described, defining a therapy target that characterizes source 108, e.g., in terms of position, spatial size and/or spatial shape, may permit selection of therapy parameters to more specifically target the source and more effectively counteract the beta band oscillations emitted from the source. Different signal characteristics may be used to characterize sources for different therapies, for example, a different frequency band may be of interest for a different therapy.

In some instances, the source may exhibit a detectable signal characteristic in the time domain rather than the frequency domain. For instance, an instantaneous or time-averaged signal amplitude of an LFP that exceeds or is below a high or low threshold value, respectively, may be monitored in response to therapy to determine a spatial extent of source 108. As another example, a waveform morphology, as may be determined based on template matching or some other mechanism, may be monitored to determine spatial extent of source 108. As yet another illustration, EEG signals may be used to determine whether epileptic-type activity is responding to stimulation to define spatial extent of the source.

Thus, while the beta band oscillations are used as an example, any sensed characteristic of a signal in the time or frequency domains that is indicative of responsiveness to stimulation (e.g., responsiveness of affected tissue to stimulation) may be monitored to define a therapy target. Algorithms for defining a therapy target corresponding to a spatial extent of source 108 are described with reference to FIGS. 4A-10.

In some examples, the therapy target may be defined during a programming session before the implantation of IMD 110, including during implantation of lead 114 in patient, as shown in FIG. 1A. As shown in FIG. 1A, a motor 122 may be used to position lead 114 and the therapy target may be defined during movement of lead 114 within patient 104 by, for example, motor 122. In some examples, the therapy target may be defined during a programming session after implantation of IMD 110 and lead 114 in patient 104, as shown in FIG. 1B. The therapy target may also be subsequently defined at later times to monitor for changes in the therapy target and/or movement of lead 114. For example, a therapy target may be initially defined at an initial definition time and a therapy target may be defined at a later definition time. Changes in definition from the initial time to the later time may indicate changes in source 108, such as, for example, growth or retraction of source 108, and/or may indicate movement of lead 114 with respect to source 108. Although system 102 is described as including an IMD 110 and a separate programmer 120, system 102 may also be implemented with a device not intended to be implanted in patient 104 and/or without a separate programmer 120. For example, system 102 may be used in a procedure including implantation of lead 114 in brain 106, definition of the therapy target corresponding to source 108, delivery of therapy based on the therapy target definition, such as, for example, forming a lesion in brain 106 corresponding to the therapy target definition and thus corresponding to source 108, and removal of lead 114 from brain 106. Such a procedure may, for example, use motor 122 for positioning of lead 114 during the procedure including, for example, during definition of the therapy target and/or during forming of the lesion. Defining a therapy target corresponding to a spatial extent of source 108 may further be used for other therapeutic approaches including, for example, plasticity inductions, drug infusions, and/or more broadly mapping states and extents of brain dysfunction.

In some examples, the process may be performed while simultaneously forming a lesion. For example, the process may be performed to monitor the source while forming the lesion. In other examples, the process may be performed to determine a 3-dimensional mapping of the source, the mapping may be stored, and the lesion may be formed based on the stored mapping.

IMD 110 may be implanted within a subcutaneous pocket above the clavicle, or, alternatively, the abdomen, back or buttocks of patient 104, on or within a cranium or at any other suitable site within patient 104. Generally, IMD 110 is constructed of a biocompatible material that resists corrosion and degradation from bodily fluids. IMD 110 may comprise a hermetic housing to substantially enclose components, such as a controller, therapy module, and memory.

Implanted lead extension 116 may be coupled to IMD 110 via a connector (also referred to as a connector block or a header) of IMD 110. In the example of FIG. 1B, after IMD 110 has been implanted, e.g., chronically, lead extension 116 traverses from the implant site of IMD 110 and along the neck of patient 104 to the cranium of patient 104 to access brain 106. Lead 114 may be implanted within the right or left hemisphere of patient 104 in order to deliver electrical stimulation to one or more regions of brain 106, which may be selected based on the patient condition or disorder controlled by therapy system 102, including one or more regions suspected or concluded to include source 108. The specific target tissue site and the stimulation electrodes used to deliver stimulation to the target tissue site, however, may be selected, e.g., using the algorithms described herein, e.g., with respect to FIGS. 4A-10. Other implant sites for lead 114 and IMD 110 are contemplated. For example, IMD 110 may be implanted on or within the cranium of patient 104, in some examples.

Lead 114 may be positioned to deliver electrical stimulation to one or more target tissue sites within brain 106 including source 108 to manage patient symptoms associated with a movement disorder of patient 104. Lead 114 may be implanted to position electrodes 118a, 118b, 118c, and 118d at desired locations of brain 106 through respective holes in the patient's cranium. Lead 114 may be placed at any location within brain 106 such that at least one of electrodes 118a, 118b, 118c, 118d are capable of providing electrical stimulation to target tissue sites within brain 106 during treatment. For example, electrodes 108a, 108b, 108c, and 108d may be surgically implanted under the dura mater of brain 106 or within the cerebral cortex of brain 106 via a burr hole in the cranium of patient 104, and electrically coupled to IMD 110 via lead 114.

Example techniques for delivering therapy to manage a movement disorder are described in U.S. Patent Application Publication No. 2009/0099627 by Molnar et al., entitled, "THERAPY CONTROL BASED ON A PATIENT MOVEMENT STATE," filed on Sep. 25, 2008, which is incorporated herein by reference in its entirety. In some examples described by U.S. Patent Application Publication No. 2009/0099627 by Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 104 initiate movement or maintain movement, and upon detecting a rest state of patient 104, therapy delivery may be deactivated or otherwise modified.

In the example shown in FIGS. 1A and 1B, electrodes 118a, 118b, 118c, and 118d of lead 114 are shown as ring electrodes. Ring electrodes may be used in DBS applications because they are relatively simple to program and are capable of delivering an electrical field to any tissue adjacent to electrodes 118a, 118b, 118c, and 118d. In other examples, electrodes 118a, 118b, 118c, and 118d may have different configurations. For example, in some examples, at least some of the electrodes 118a, 118b, 118c, and 118d of lead 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. For example, electrode segments may be positioned at the same axial position but at different angular positions around the circumference of the lead. Sets of electrode segments may be provided at different axial positions, e.g., such that sets of two, three, four or more electrode segments form discontinuous rings or partial rings around the lead circumference at different axial positions. In some examples, ring electrodes and segmented electrodes may be combined on a lead, such that ring electrodes are formed at some axial positions and segmented electrodes are formed at other axial positions. An example is a 1-3-3-1 configuration in which a first ring electrode is formed on a lead at a first axial position, a first set of three electrode segments are formed at a second axial position, a second set of three electrode segments are formed at a third axial position and a second ring electrode is formed at a fourth axial position, where the first, second, third and fourth positions are arranged in axial order along the length of the lead.

With segmented electrodes, electrical stimulation may be directed in a specific direction from lead 114 to enhance therapy target definition, as will be described with reference to FIGS. 4A-10 and FIGS. 6A and 6B in particular, and/or therapy efficacy and reduce possible adverse side effects from stimulating a larger volume of tissue. In some examples, a housing of IMD 110 may include one or more stimulation and/or sensing electrodes. In alternative examples, lead 114 may have shapes other than elongated cylinders as shown in FIGS. 1A and 1B. For example, lead 114 may be a paddle lead, spherical lead, bendable lead, or any other type of shape effective in treating patient 104, including defining a therapy target corresponding to source 108 and delivering therapy based on the therapy target definition, as described with reference to FIGS. 4A-10, and/or minimizing invasiveness of lead 114.

In the example shown in FIGS. 1A and 1B, IMD 110 includes a memory (shown in FIG. 2) to store therapy target definition programs for defining a therapy target and may, after defining the therapy target, store one or more therapy programs that may each define a set of therapy parameters for delivering therapy based on the therapy target definition. In some examples, IMD 110 may select a therapy program from the memory based on various parameters, such as a detected patient activity level, a detected patient state, based on the time of day, and the like. IMD 110 may generate electrical stimulation based on the selected therapy program to manage the patient symptoms associated with a movement disorder.

In some examples, defining the therapy target may comprise defining parameters for delivering therapy, including selecting electrodes for delivery of electrical stimulation and/or selecting intensities of electrical stimulation which may be a function of amplitude, pulse width, and pulse rate. The particular electrodes and stimulation intensity levels that are selected in accordance with examples of this disclosure may spatially characterize an oscillation source and also serve, directly or indirectly, as parameters for delivery of electrical stimulation therapy. Hence, in such an example, sensed signals and intensities selected to define the therapy parameters also may be representative of a therapy target that is a function of a spatial extent of an oscillatory source. In other examples, the therapy target may be defined and then the parameters may be selected based on the therapy target definition.

During a trial stage in which IMD 110 is evaluated to determine whether IMD 110 provides efficacious therapy to patient 104, a plurality of therapy target definition programs and/or therapy programs may be tested and evaluated for efficacy. Therapy target definition programs and/or therapy programs may be selected for storage within IMD 110 based on the results of the trial stage.

During chronic therapy in which IMD 110 is implanted within patient 104 for delivery of therapy on a non-temporary basis, IMD 110 may generate and deliver stimulation signals to patient 104 according to different therapy target definition programs and/or therapy programs. In addition, in some examples, patient 104 may modify the value of one or more therapy parameter values within a single given program or switch between programs in order to alter the efficacy of the therapy as perceived by patient 104 with the aid of programmer 120. The memory of IMD 110 may store instructions defining the extent to which patient 104 may adjust therapy parameters, switch between programs, or undertake other therapy adjustments. Patient 104 may generate additional programs for use by IMD 110 via external programmer 120 at any time during therapy or as designated by the clinician.

External programmer 120 may wirelessly communicate with IMD 110 as needed to provide or retrieve therapy information. Programmer 120 may be an external computing device that the user, e.g., the clinician and/or patient 104, may use to communicate with IMD 110. For example, programmer 120 may be a clinician programmer that the clinician uses to communicate with IMD 110 and program one or more target definition programs and/or one or more therapy programs for IMD 110. Alternatively, programmer 120 may be a patient programmer that allows patient 104 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 110.

Programmer 120 may be a hand-held computing device with a display viewable by the user and an interface for providing input to programmer 120 (i.e., a user input mechanism). For example, programmer 120 may include a small display screen (e.g., a liquid crystal display (LCD) or a light emitting diode (LED) display) that presents information to the user. In addition, programmer 120 may include a touch screen display, keypad, buttons, a peripheral pointing device or another input mechanism that allows the user to navigate though the user interface of programmer 120 and provide input. If programmer 120 includes buttons and a keypad, the buttons may be dedicated to performing a certain function, i.e., a power button, or the buttons and the keypad may be soft keys that change in function depending upon the section of the user interface currently viewed by the user. Alternatively, a screen of programmer 120 may be a touch screen that allows the user to provide input directly to the user interface shown on the display. The user may use a stylus or a finger to provide input to the display.

In other examples, programmer 120 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 120. A wireless adapter coupled to the computing device may enable secure communication between the computing device and IMD 110 or a hardwired connection may be provided.

When programmer 120 is configured for use by the clinician, programmer 120 may be used to transmit initial programming information to IMD 110. This initial information may include hardware information, such as the type of lead 114 and the electrode arrangement, the position of lead 114 within brain 106, the configuration of electrodes 118, initial programs defining therapy target definition programs and/or therapy programs to be implemented based on therapy target definitions, and any other information the clinician desires to program into IMD 110. Programmer 120 may also be capable of completing functional tests (e.g., measuring the impedance of electrodes 118a, 118b, 118c, and 118d).

The clinician may also store therapy target definition programs and/or therapy programs within IMD 110 with the aid of programmer 120. During a programming session, the clinician may determine one or more target therapy definition programs and/or therapy programs that may provide efficacious therapy to patient 104 to address symptoms associated with the patient condition, and, in some cases, specific to one or more different patient states, such as a sleep state, movement state or rest state. During the programming session, patient 104 may provide feedback to the clinician as to the efficacy of the specific program being evaluated or the clinician may evaluate the efficacy based on one or more physiological parameters of patient 104 (e.g., signals sensed from the brain, muscle activity or muscle tone). Programmer 120 may assist the clinician in the creation/identification of target therapy definition programs and/or therapy programs by providing a methodical system for identifying potentially beneficial therapy target definition programs and/or therapy programs, including programs including therapy parameters based on a therapy target definition.

Programmer 120 may also be configured for use by patient 104. When configured as a patient programmer, programmer 120 may have limited functionality (compared to a clinician programmer) in order to prevent patient 104 from altering critical functions of IMD 110 or applications that may be detrimental to patient 104. In this manner, programmer 120 may only allow patient 104 to adjust values for certain therapy parameters or set an available range of values for a particular therapy parameter.

Programmer 120 may also provide an indication to patient 104 when therapy is being delivered, when patient input has triggered a change in therapy or when the power source within programmer 120 or IMD 110 needs to be replaced or recharged. For example, programmer 120 may include an alert LED, may flash a message to patient 104 via a programmer display, generate an audible sound or somatosensory cue to confirm patient input was received, e.g., to indicate a patient state or to manually modify a therapy parameter.

Programmer 120 may be configured to communicate to IMD 110 and, optionally, another computing device, via wireless communication. Programmer 120, for example, may communicate via wireless communication with IMD 110 using radio frequency (RF) or inductive telemetry techniques according to any proprietary or industry standard communication protocols known in the art. Programmer 120 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 120 may also communicate with other programming or computing devices via exchange of removable media, such as magnetic or optical disks, memory cards or memory sticks. Further, programmer 120 may communicate with IMD 110 and another programmer via remote telemetry techniques known in the art, communicating via a local area network (LAN), wide area network (WAN), public switched telephone network (PSTN), or cellular telephone network, for example.

Therapy system 102 may be implemented to provide chronic stimulation therapy to patient 104 over the course of several months or years. However, system 102 may also be employed on a trial basis to evaluate therapy before committing to full implantation. If implemented temporarily, some components of system 102 may not be implanted within patient 104. For example, patient 104 may be fitted with an external medical device, such as a trial stimulator, rather than IMD 110. The external medical device may be coupled to percutaneous leads or to implanted leads via a percutaneous extension. If the trial stimulator indicates DBS system 102 provides effective treatment to patient 104, the clinician may implant a chronic stimulator within patient 104 for relatively long-term treatment. As another example, an external medical device may be used in combination with lead 114 to define a therapy target and deliver therapy in a single procedure without long-term treatment. For example, lead 114 may be implanted within brain 106 of patient 104 using, for example a motor 122, as shown in FIG. 1A, and system 102 may be used to define a therapy target and deliver therapy in the form of a lesion corresponding to the therapy target definition, and lead 114 may be removed from brain 106 of patient 104.

Figure 2:
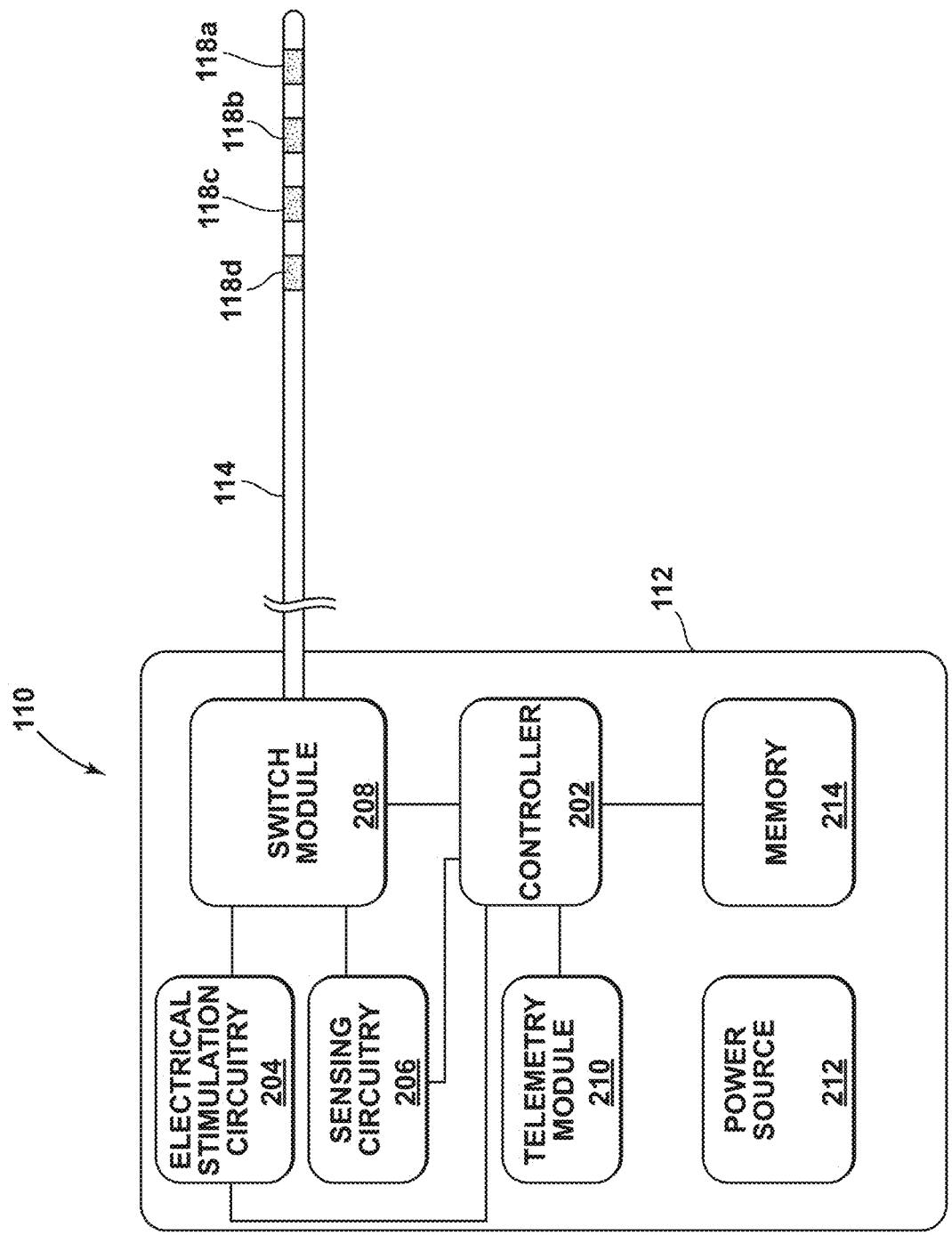
FIG. 2 is a functional block diagram illustrating components of an example medical device.

FIG. 2 is a functional block diagram illustrating components of an example IMD 110. In the example shown in FIG. 2, IMD 110 includes controller 202, memory 214, electrical stimulation circuitry 204, sensing circuitry 206, switch module 208, telemetry module 210, and power source 212. Memory 214 may include any volatile or non-volatile media, such as a random access memory (RAM), read only memory (ROM), non-volatile RAM (NVRAM), electrically erasable programmable ROM (EEPROM), flash memory, and the like. Memory 214 may store computer-readable instructions that, when executed by controller 202, cause IMD 110 to perform various functions.

Memory 214 may store therapy target definition programs for defining a therapy target as described with reference to FIGS. 4A-10, and/or therapy programs for delivering therapy based on therapy target definitions. Memory 214 may store programs in separate memories within memory 214 or separate areas within memory 214. In addition, in some examples, memory 214 may store a bioelectrical brain signal sensed via at least some of the stored sense electrode combinations and/or one or more frequency band characteristics of the bioelectrical brain signals. Each stored therapy program defines a particular set of electrical stimulation parameters (also referred to as therapy parameters) such as a stimulation electrode combination, electrode polarity, current or voltage amplitude, pulse width, whether cycling is on/off, waveform shape, and pulse rate to be applied based on a therapy target definition. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Memory 214 may store sense and stimulation electrode combinations that identify sense electrode combinations and associated stimulation electrode combinations. As described above, in some examples, the sense and stimulation electrode combinations may include the same subset of electrodes or may include different subsets of electrodes. Thus, memory 214 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by controller 202.

In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 106 in order to mitigate any irregular oscillations or other irregular brain activity within the tissue site associated with the sense electrode combination.

Memory 214 may store operating instructions to guide general operation of IMD 110 under control of controller 202, and may include instructions for measuring the impedance of electrodes 118 and/or determining the distance between electrodes 118.

Electrical stimulation circuitry 204, under the control of controller 202, may generate stimulation signals for delivery to patient 104 via selected combinations of electrodes 118. As described in further detail with respect to FIGS. 4A-10, electrical stimulation circuitry 204 may generate stimulation signals for delivery to patient 104 to define a therapy target. In some examples, electrical stimulation circuitry 204 may also generate stimulation signals for delivery to patient to deliver therapy based on the therapy target definition.

Controller 202 may include any one or more of a microprocessor, a controller, a digital signal processor (DSP), an application specific integrated circuit (ASIC), a field-programmable gate array (FPGA), discrete logic circuitry, and the functions attributed to controller 202 herein may be embodied as firmware, hardware, software or any combination thereof. Controller 202 may control electrical stimulation circuitry 204 according to therapy target definition programs stored in memory 214, and/or according to therapy programs stored in memory 214 and a therapy target definition and/or defined parameters (which may be representative of the therapy target definition or derived from the therapy target definition), to apply particular stimulation parameter values specified by one or more of programs, such as amplitude, pulse width, and pulse rate.

In the example shown in FIG. 2, the set of electrodes 118 includes electrodes 118a, 118b, 118c, and 118d. Controller 202 also controls switch module 208 to apply the stimulation signals generated by electrical stimulation circuitry 404 to selected combinations of electrodes 118. In particular, switch module 208 may couple stimulation signals to selected conductors within lead 114, which, in turn, deliver the stimulation signals across selected electrodes 118. Switch module 208 may be a switch array, switch matrix, multiplexer, or any other type of switching module configured to selectively couple stimulation energy to selected electrodes 118 and to selectively sense bioelectrical brain signals with selected electrodes 118. Hence, electrical stimulation circuitry 204 is coupled to electrodes 118 via switch module 208 and conductors within lead 114. In some examples, however, IMD 110 does not include switch module 208. Instead, IMD 110 may include a dedicated voltage or current source for electrical stimulation circuitry and a sink for each electrode. Controller 202 may control the source and sinks to apply the electrical stimulation signals generated by electrical stimulation circuitry 202 to selected combinations of electrodes 118.

Electrical stimulation circuitry 204 may be a single channel or multi-channel electrical stimulation circuitry. In particular, electrical stimulation circuitry 204 may be capable of delivering a single stimulation pulse, multiple stimulation pulses, or a continuous signal at a given time via a single electrode combination or multiple stimulation pulses at a given time via multiple electrode combinations. In some examples, however, electrical stimulation circuitry 204 and switch module 208 may be configured to deliver multiple channels on a time-interleaved basis. For example, switch module 208 may serve to time divide the output of electrical stimulation circuitry 204 across different electrode combinations at different times to deliver multiple programs or channels of stimulation energy to patient 104.

Sensing circuitry 206, under the control of controller 202, may sense bioelectrical brain signals and provide the sensed bioelectrical brain signals to controller 202. Controller 202 may control switch module 208 to couple sensing circuitry 206 to a selected combinations of electrodes 118, i.e., a sense electrode combination. In this way, IMD 110 is configured such that sensing circuitry 206 may sense bioelectrical brain signals with a plurality of different sense electrode combinations. Switch module 208 may be electrically coupled to the selected electrodes 118 via the conductors within lead 114, which, in turn, deliver the bioelectrical brain signal sensed across the selected electrodes 118 to sensing circuitry 206. The bioelectrical brain signal may include electrical signals that are indicative of electrical activity within brain 106 of patient 104.

Although sensing circuitry 206 is incorporated into a common housing with electrical stimulation circuitry 204 and controller 202 in FIG. 2, in other examples, sensing circuitry 206 may be in a separate housing from IMD 110 and may communicate with controller 202 via wired or wireless communication techniques. Example bioelectrical brain signals include, but are not limited to, a signal generated from local field potentials within one or more regions of brain 104. EEG and ECoG signals are examples of local field potentials that may be measured within brain 104. However, local field potentials may include a broader genus of electrical signals within brain 106 of patient 104. Controller 202 may analyze a plurality of bioelectrical brain signals, e.g., by determining relative values of signal characteristics (e.g., potentials or frequency domain characteristics) of the biosignal. Beta band signals and/or gamma band signals may also be measured within brain 104 and may result, for example, from a source of beta and/or gamma oscillations, such as source 108, within brain 106.

Telemetry module 210 supports wireless communication between IMD 110 and an external programmer 120 or another computing device under the control of controller 202. Controller 202 of IMD 110 may receive, updates to therapy definition programs and/or updates to therapy programs, from programmer 120 via telemetry module 210. The updates to the therapy programs may be stored within memory 214. Telemetry module 210 may send information related to a therapy target definition to programmer 120 via telemetry module 210. For example, telemetry module 210 may send an initial therapy target definition to programmer 120. Telemetry module 210 may also send an updated therapy target definition to programmer 120 to indicate changes to source 108 and/or movement of lead 114 with respect to source 108. Telemetry module 210 in IMD 110, as well as telemetry modules in other devices and systems described herein, such as programmer 120, may accomplish communication by radiofrequency (RF) communication techniques. In addition, telemetry module 210 may communicate with external medical device programmer 120 via proximal inductive interaction of IMD 110 with programmer 120. Accordingly, telemetry module 210 may send information to external programmer 120 on a continuous basis, at periodic intervals, or upon request from IMD 110 or programmer 120.

In some examples, IMD 110 and/or programmer 120 may define a therapy target and/or select therapy parameters based on the therapy target definition. For example, IMD 110 may define the therapy target and select therapy parameters based on the therapy target definition. In other examples, IMD 110 may define the therapy target and send the therapy target definition to programmer 120 and programmer 120 may select therapy parameters based on the therapy target definition and send the selected therapy parameters to IMD 110. In some examples, IMD 110 may deliver and/or sense signals and send information indicative of the delivered and/or sensed signals to programmer 120 and programmer 120 may define the therapy target, select therapy parameters based on the therapy target definition, and send the selected therapy parameters to IMD 110. In some examples, IMD 110 may deliver and/or sense signals and send information indicative of the delivered and/or sensed signals to programmer 120, programmer 120 may define the therapy target and send the therapy target definition to IMD 110, and IMD 110 may select therapy parameters based on the therapy target definition. One or more modules for defining a therapy target and/or selecting therapy parameters based on the therapy target definition may be stored and/or executed by one or more of IMD 110, programmer 120, and/or any other suitable component. In some examples, a user may select one or more therapy parameters based on a therapy target definition.

In some examples, selecting therapy parameters based on defined parameters may comprise selecting the defined parameters. In other examples, selecting therapy parameters based on defined parameters may include selecting parameters that are a function of the defined parameters but are not the same as the defined parameters. For example, defining the therapy target may comprise defining parameters for delivering therapy, including, for example, selecting electrodes for delivery of electrical stimulation and/or selecting intensities of electrical stimulation delivered by the selected electrodes. The selected electrodes and selected intensities may define the therapy target and directly form parameters for delivery of electrical stimulation therapy. In other examples, the therapy target may be defined and then the stimulation parameters may be selected based on the therapy target definition.

Power source 212 may deliver operating power to various components of IMD 110. Power source 212 may include a small rechargeable or non-rechargeable battery and a power generation circuit to produce the operating power. Recharging may be accomplished through proximal inductive interaction between an external charger and an inductive charging coil within IMD 110. In some examples, power requirements may be small enough to allow IMD 110 to utilize patient motion and implement a kinetic energyscavenging device to trickle charge a rechargeable battery. In other examples, traditional batteries may be used for a limited period of time.

Figure 3:
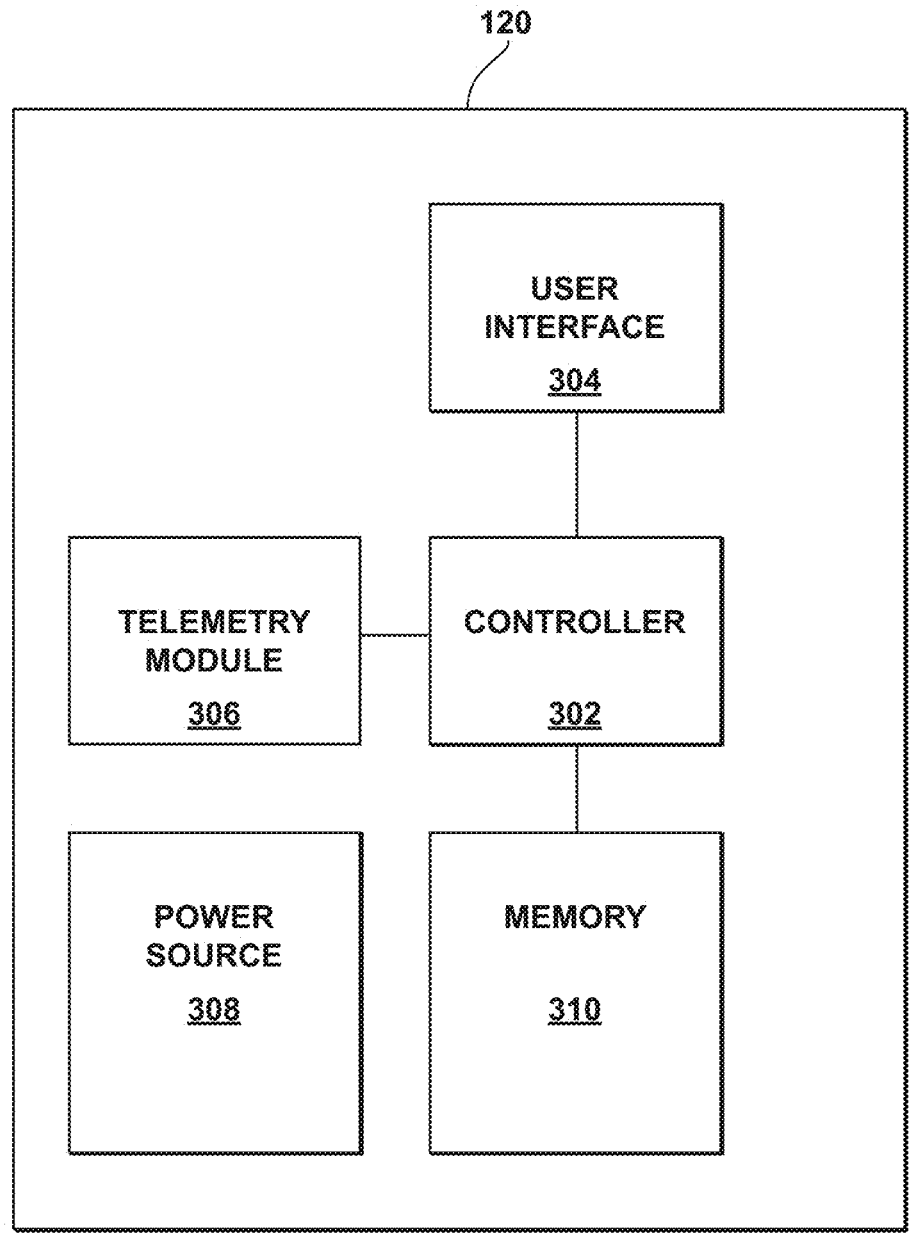
FIG. 3 is a functional block diagram illustrating components of an example medical device programmer.

FIG. 3 is a functional block diagram illustrating components of an example medical device programmer 120, which includes controller 302, memory 310, telemetry module 306, user interface 304, and power source 308. Controller 302 controls user interface 304 and telemetry module 306, and stores and retrieves information and instructions to and from memory 310. Programmer 120 may be configured for use as a clinician programmer or a patient programmer. Controller 302 may comprise any combination of one or more processors including one or more microprocessors, DSPs, ASICs, FPGAs, or other equivalent integrated or discrete logic circuitry. Accordingly, controller 302 may include any suitable structure, whether in hardware, software, firmware, or any combination thereof, to perform the functions ascribed herein to controller 302.

A user, such as a clinician or patient 104, may interact with programmer 120 through user interface 304. User interface 304 may include a display, such as a LCD or LED display or other type of screen, to present information related to a therapy target definition and/or a therapy, such as an image depicting a 3-dimensional representation of the spatial extent (e.g., size and/or shape) of source 108 based on a therapy target defined by system 102. In addition, user interface 304 may include an input mechanism to receive input from the user. The input mechanisms may include, for example, buttons, a keypad (e.g., an alphanumeric keypad), a peripheral pointing device or another input mechanism that allows the user to navigate though user interfaces presented by controller 302 of programmer 120 and provide input.

If programmer 120 includes buttons and a keypad, the buttons may be dedicated to performing a certain function, i.e., a power button, or the buttons and the keypad may be soft keys that change in function depending upon the section of the user interface currently viewed by the user. Alternatively, a screen of programmer 120 may be a touch screen that allows the user to provide input directly to the user interface shown on the display. The user may use a stylus or a finger to provide input to the display. In other examples, user interface 304 also includes audio circuitry for providing audible instructions or sounds to patient 104 and/or receiving voice commands from patient 104, which may be useful if patient 104 has limited motor functions. Patient 104, a clinician or another user may also interact with programmer 120 to manually select therapy programs, generate new therapy programs, modify therapy programs through individual or global adjustments, and transmit the new programs to IMD 110. For example, although therapy programs may be based on a therapy target definition, patient 104 may have the option to choose between different programs based on the therapy target definition and/or make adjustments to programs.

In some examples, at least some of the control of therapy delivery by IMD 110 may be implemented by controller 302 of programmer 120. For example, in some examples, controller 302 may control delivery of stimulation signals by IMD 110 and receive bioelectrical brain signals, in response to the delivered signals, from IMD 110 or from a sensing circuitry that is separate from IMD 110. The separate sensing circuitry may, but need not be, implanted within patient 110. In some examples, controller 302 may define a therapy target based on the received signals, e.g., by implementing an algorithm similar or identical to that implemented by IMD 110 and stored by memory 211 of IMD 110 and described with reference to FIGS. 4A-10. Controller 202 of IMD 110 may receive the signal from programmer 120 via its respective telemetry module 210 (FIG. 2).

Memory 310 may include instructions for operating user interface 304 and telemetry module 306, and for managing power source 308. Memory 310 may also store any therapy data retrieved from IMD 110 during the course of therapy. The clinician may use this therapy data to determine the progression of the patient condition in order to predict future treatment. Memory 310 may include any volatile or non-volatile memory, such as RAM, ROM, EEPROM or flash memory. Memory 310 may also include a removable memory portion that may be used to provide memory updates or increases in memory capacities. A removable memory may also allow sensitive patient data to be removed before programmer 120 is used by a different patient.

Wireless telemetry in programmer 120 may be accomplished by RF communication or proximal inductive interaction of external programmer 120 with IMD 110. This wireless communication is possible through the use of telemetry module 306, which may communicate with a proprietary protocol or industry-standard protocol such as using the Bluetooth specification set. Accordingly, telemetry module 306 may be similar to the telemetry module contained within IMD 110. In alternative examples, programmer 120 may be capable of infrared communication or direct communication through a wired connection. In this manner, other external devices may be capable of communicating with programmer 120 without needing to establish a secure wireless connection.

Power source 308 may deliver operating power to the components of programmer 120. Power source 308 may include a battery and a power generation circuit to produce the operating power. In some examples, the battery may be rechargeable to allow extended operation. Recharging may be accomplished by electrically coupling power source 308 to a cradle or plug that is connected to an alternating current (AC) outlet. In addition, recharging may be accomplished through proximal inductive interaction between an external charger and an inductive charging coil within programmer 120. In other examples, traditional batteries (e.g., nickel cadmium or lithium ion batteries) may be used. In addition, programmer 120 may be directly coupled to an alternating current outlet to operate. Power source 308 may include circuitry to monitor power remaining within a battery. In this manner, user interface 304 may provide a current battery level indicator or low battery level indicator when the battery needs to be replaced or recharged. In some cases, power source 308 may be capable of estimating the remaining time of operation using the current battery.

Figure 4A:
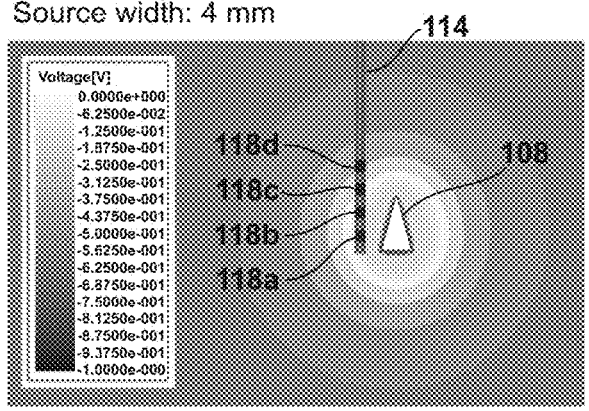
FIGS. 4A and 4B are conceptual diagrams illustrating example configurations for sensing electrical signals at a plurality of different positions within a brain of a patient.
Figure 4B:
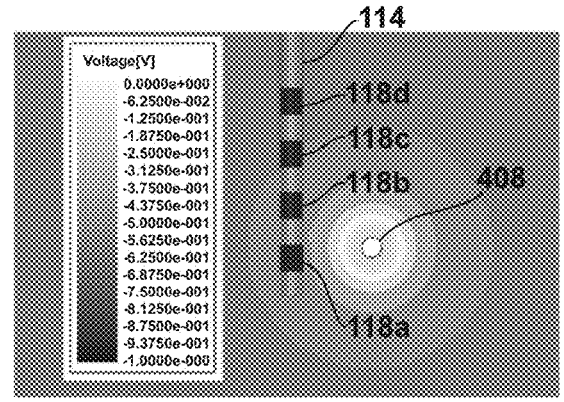

FIGS. 4A and 4B are conceptual diagrams illustrating example configurations for sensing electrical signals at a plurality of different positions within brain 106 of patient 104.

As shown in FIG. 4A, lead 114 with electrodes, 118a, 118b, 118c, and 118d of lead 114 may be positioned within brain 106 adjacent to triangular source 108, as also illustrated in FIGS. 1A and 1B. Source 108 may be considered triangular in the sense that at least a cross-section of source 108 extending in a radial direction away from lead 114 may be substantially triangular in shape. Conventional techniques for measuring source 108 may not readily be able to determine such a shape for source 108 and/or distinguish between different shapes of sources. Each of electrodes 118a, 118b, 118c, and 118d may sense local field potentials at a plurality of different positions within brain 106, corresponding to the positions of each of electrodes 118a, 118b, 118c, and 118d before electrical stimulation is delivered.

Although each of electrodes 118a and 118b are described as single electrodes, electrodes 118a and 118b may each correspond to a group of electrodes, each group corresponding to a position within brain 106. EEG and ECoG signals are examples of local field potentials that may be measured within brain 104. However, local field potentials may include a broader genus of electrical signals within brain 106 of patient 104. In the example of FIG. 4A, triangular source 108 has a thickness of 1 mm, a height of 6 mm, and a width of 4 mm.

As shown in FIG. 4B, lead 114 with electrodes, 118a, 118b, 118c, and 118d of lead 114 may be positioned within brain 106 adjacent to spherical source 408. Source 408 may be considered spherical in the sense that at least a cross-section of source 408 extending in a radial direction away from lead 114 may be substantially circular in shape. Conventional techniques for measuring source 108 may not readily be able to determine such a shape for source 408 and/or distinguish between different shapes of sources. Each of electrodes 118a, 118b, 118c, and 118d may sense local field potentials at a plurality of different positions within brain 106, corresponding to the positions of each of electrodes 118a, 118b, 118c, and 118d at a time at which electrical stimulation is not delivered. In the example of FIG. 4B, spherical source 408 has a thickness of 0.5 mm.

As shown in each of FIGS. 4A and 4B, electrical signals may be sensed at a plurality of different positions when electrical stimulation is not delivered. For example, sensing circuitry 206 may sense electrical signals at positions corresponding to each of electrodes, electrode groups, or electrode segments 118a, 118b, 118c, 118d along the length of lead 114. In some examples, the sensing may be performed in bipolar fashion such that the sensed local field potentials are measured as a comparison to a reference local field potential such that the reference local field potential is designated as having a value of zero and the values of the sensed local field potentials are based on the deviation from the reference. The reference local field potential may be, for example, a local field potential measured at a position not affected by source 108 and the sensed local field potentials may be measured as a deviation from that reference local field potential. The reference local field potential may be that measured at any suitable position. As shown in FIGS. 4A and 4B, a reference local field potential may be designated as 0 V and the other local field potentials may be measured with reference to the reference local field potential. In the illustrated example, a position closest to source 108 may be expected to have the greatest deviation from the reference.

The local field potential may be characterized by the magnitude or amplitude of the sensed signal. Alternatively, the local field potential may be characterized by the spectral power within a specific frequency band (e.g., beta band).

Figure 5:
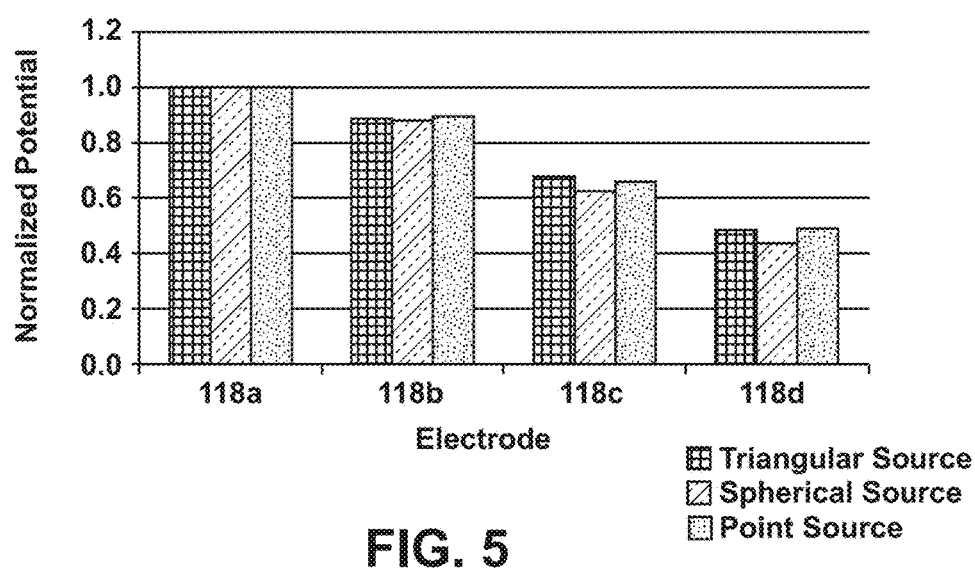
FIG. 5 is a graph illustrating electrical signals sensed at the plurality of different positions within a brain of a patient for each of a triangular source, a spherical source, and a point source.

FIG. 5 is a graph illustrating electrical signals sensed at the plurality of different positions within a brain of a patient for each of triangular source 108, shown in FIG. 4A, spherical source 408, shown in FIG. 4B, and a point source (not shown).

In some examples, the sensed local field potentials, as described with reference to FIGS. 4A and 4B, may be normalized based on the position with the sensed local field potential with the greatest deviation from the reference. For example, in the illustrated example, for the triangular source illustrated in FIG. 4A, the position associated with 118a may be associated with the local field potential with the greatest deviation from the reference such that it is normalized as "1.0." The position associated with 118b may be associated with the local field potential with a deviation from the reference that is approximately 0.9 of that of the position associated with 118a, such that it is normalized to "0.9." Likewise, the sensed local field potentials at positions corresponding to 118c and 118d may have a deviation from the reference that is approximately 0.7 and 0.5 of that of the position associated with 118a, and may thus be normalized to be approximately "0.7" and "0.5."

Examples of normalized local field potentials for each of a spherical and point source are also shown in the graph of FIG. 5.

As shown in FIG. 5, the profile of normalized local field potentials sensed at each of electrodes 118a, 118b, 118c, and 118d are substantially similar adjacent to each of the differently shaped sources.

Because the profile of normalized local field potentials sensed at each of electrodes 118a, 118b, 118c, and 118d may be substantially similar adjacent to each of the differently shaped sources, as illustrated with reference to FIGS. 4A, 4B, and 5, sensing these local field potentials alone may not allow for distinguishing the shapes of the different sources and additional information may be needed to identify a shape for a particular source and/or therapy parameters appropriate for a particular source shape. Characteristics of local field potentials between pairs of electrodes (e.g., electrode pairs 118a-118b or 118b-118c) may also be similar indicating that additional information may be needed to characterize the position and spatial extent of the source. More than one local field potential characteristic may be used to characterize the source (e.g., ratio of the power in two different frequency bands).

In some examples, the positions at which the sensed local field potentials are over a threshold amount or are the highest when compared to other positions, for example, the positions corresponding to 118a and 118b for each of the example triangular source, spherical source, and point source, may be of particular interest for additional analysis as the local field potentials may indicate that positions corresponding to each of electrodes 118a and 118b may be adjacent to the source. In some examples, the positions with the highest sensed local field potentials may be selected for additional analysis. In other examples, each of the positions may be selected for additional analysis. For example, obtaining the local field potential power profiles as shown may allow controller 202 and/or controller 302 to select those electrodes with the highest sensed power for further analysis.

Figure 6A:
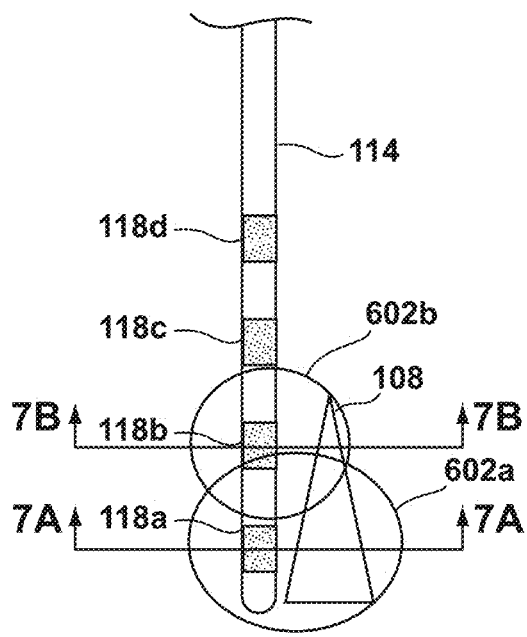
FIGS. 6A, 6B, and 6C are diagrams illustrating example electrode configurations for delivering electrical stimulation at a plurality of different intensities at each of a plurality of different positions within a brain of a patient and sensing electrical signals at each of the different positions in response to the electrical stimulation.
Figure 6B:
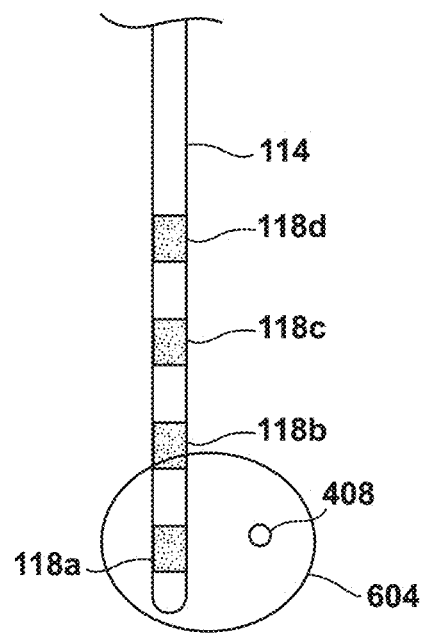
Figure 6C:
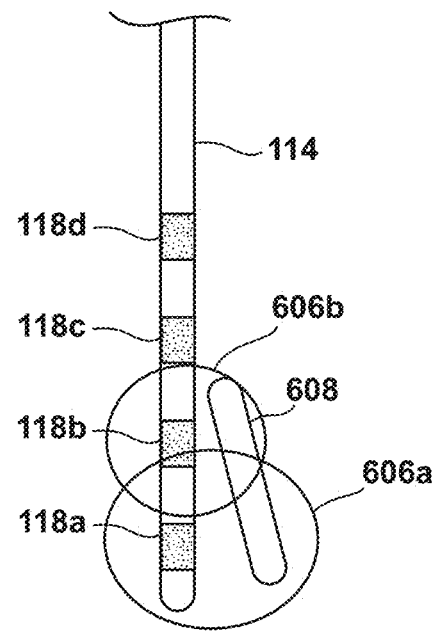

FIGS. 6A, 6B, and 6C are diagrams illustrating example electrode configurations for delivering electrical stimulation at a plurality of different intensities at each of a plurality of different positions within brain 106 of patient 104 and sensing electrical signals at each of the different positions in response to the electrical stimulation delivered at each of the different intensities. Electrode configurations, such as those shown in FIGS. 6A, 6B and 6C, may permit spatial definition of a therapy target based on spatial characteristics of a source of signals within a brain of the patient.

FIG. 6A illustrates an example including lead 114 with electrodes 118 adjacent to triangular source 108. As described with reference to FIGS. 4A and 5, local field potentials may be sensed at each of the positions corresponding to electrodes 118a, 118b, 118c, and 118d, which may each correspond to an axial position along lead 114. In some examples where electrodes 118 are segmented electrodes, segments of electrodes 118 may also correspond to circumferential positions about lead 114, as discussed in further detail below. The sensed local field potentials may be normalized based on the highest local field potential. For example, the normalized local field potential for each of positions corresponding to 118a, 118b, 118c, and 118d may be 1.0, 0.9, 0.7, and 0.5, respectively.

Controller 202 and/or controller 302 may control electrical stimulation circuitry 204 to deliver electrical stimulation at the positions corresponding to each of electrodes 118a, 118b, 118c, and 118d. For example, controller 202 and/or controller 302 may control electrical stimulation circuitry 204 to deliver electrical stimulation via electrode 118a, 118b, 118c, and 118d. In other examples, electrical stimulation may be delivered to less that each electrode 118 based on the local field potentials sensed at the corresponding positions. For example, if a sensed local field potential was particularly low at a given position, such that it was under a threshold amount, electrical stimulation may not be delivered at that position.

Sensing circuitry 206 may sense electrical signals at each of the different positions within brain 106 of patient 104 in response to the electrical stimulation. For example, electrical signals may be sensed by each of electrodes 118a, 118b, 118c, and 118d. As previously described, although each of electrodes 118a and 118b are described as single electrodes, either or both of electrodes 118a and 118b may correspond to a group of electrodes, an electrode segment, or a group of electrode segments, each corresponding to a position within brain 106. The same or different electrodes within a group of electrodes 118a and 118b may be used for delivering electrical stimulation and/or sensing electrical signals at each of the corresponding positions.

At each selected position, corresponding to each of electrodes 118a, 118b, 118c, and 118d, electrical stimulation may be delivered at a plurality of different intensities and electrical signals may be sensed in response to the electrical stimulation delivered at each of the different intensities. For example, sensing circuitry 206 may be configured to sense beta band signals at each of the selected positions. The stimulation at different intensities may be delivered as stimulation at progressively increasing intensity levels, e.g., as a function of increasing amplitude, pulse width and/or pulse width. Electrical stimulation circuitry 204 may deliver electrical stimulation at a first intensity and sensing circuitry 206 may sense first beta band signals in response to the electrical stimulation at the first intensity. Electrical stimulation circuitry 204 may deliver electrical stimulation at a second intensity that is higher than the first intensity and sensing circuitry 206 may sense second beta band signals in response to the electrical stimulation at the second intensity. In response to the increased intensity of the electrical stimulation, the second sensed beta band signals may be lower than the first sensed beta band signals, as the increased intensity may be effective in further suppressing the beta band oscillation emitted by the source.

Electrical stimulation circuitry 204 may deliver electrical stimulation at increasing intensities until the sensed beta band signals are substantially suppressed. The level of the signal that is sensed may be spectral power of the local field potential. In some examples, the level may be of any suitable characteristic of the local field potential oscillation.

In some examples, electrical stimulation circuitry 204 may deliver electrical stimulation at a variety of intensities, sensing circuitry 206 may sense beta band signals in response to each of the delivered electrical stimulation intensities, and controller 202 and/or controller 302 may determine the responsiveness of the sensed beta band signal to the delivered electrical stimulation.

Based on the normalized local field potentials, controller 202 and/or controller 302 may determine a sequence for delivering electrical stimulation and sensing electrical signals in response to the delivered electrical stimulation at each of the positions corresponding to electrodes 118a, 118b, 118c, 118d. For example, controller 202 and/or controller 302 may determine a sequence from the position with the greatest normalized local field potential to the position with the lowest normalized local field potential. For example, the sequence may be 118a, 118b, 118c, and 118d based on the descending normalized local field potentials corresponding to those positions of 1.0, 0.9, 0.7, and 0.5, respectively. In other examples, a different sequence may be determined. In some examples, the sequence may include fewer than all of the positions corresponding to each of electrodes 118a, 118b, 118c, and 118d. For example, a local field potential and/or the normalized local field potential corresponding to one or more of the positions may be under a threshold amount such that it may be determined to not be of interest for further analysis. For example, a local field potential that is particularly small in comparison with the other positions may be determined to be too far from source 108 to be of interest.

For example, in the illustrated example, controller 202 and/or controller 302 may start by delivering electrical stimulation and sensing beta band signals in response to the delivered electrical stimulation at the position associated with 118a.

For example, controller 202 and/or controller 302 may control electrical stimulation circuitry 204 to deliver electrical stimulation at a plurality of increasing intensities and may sense beta band signals in response to the delivered electrical stimulation to determine the changes to the beta band signals in response to the delivered electrical stimulation.

Sensing circuitry 206 may sense a beta band signal at the position corresponding to 118a before electrical stimulation is delivered. The sensed beta band signal may be, for example, 10 μV. Controller 202 and/or controller 302 may control electrical stimulation circuitry 204 to deliver a first electrical stimulation at the position corresponding to electrode 118a at a first intensity of 0.5 V or 0.5 milliamp. Sensing circuitry 206 may sense the beta band signal at the position in response to the delivered electrical stimulation. The sensed beta band signal may be, for example, 9.5 μV.

At the position corresponding to electrode 118a, controller 202 and/or controller 302 may deliver electrical stimulation at increasing intensities, each time increasing the intensity, by, for example, 0.5 V or 0.5 milliamp, and sensing circuitry 206 may sense the beta band signal in response to the delivered electrical stimulation. Based on the sensed beta band signals in response to the increasing intensities of delivered electrical stimulation, controller 202 and/or controller 302 may determine the responsiveness of the beta band signal to the electrical stimulation. For example, controller 202 and/or controller 302 may continue to deliver electrical stimulation at intensities increasing by, for example, 0.5 V or 0.5 milliamp, until increasing the intensity no longer results in a lower beta band signal. For example, in the example described above, controller 202 and/or controller 302 may deliver electrical stimulation at 0.5V or 0.5 milliamp, 1.0 V or 1.0 milliamp, 1.5 V or 1.5 milliamps, etc., at increasing intervals of 0.5 V or 0.5 milliamp, up to 10 V or 10 milliamps, and the sensed beta band signal may decrease in response to each increase in intensity. When electrical stimulation is delivered at 10 V or 10 milliamps, the sensed beta band signal in response to the electrical stimulation may be, for example, 2 μV. Controller 202 and/or controller 302 may then increase the intensity again, to 10.5 V or 10.5 milliamps. This time, the sensed beta band signal that results may not decrease but may remain at 2 μV. Controller 202 and/or controller 302 may increase the intensity again, to 11 V or 11 milliamps. The resulting beta band signal may, again, remain at 2 μV. Because increasing the intensity of electrical stimulation to 10 V or 10 milliamps decreases the resulting beta band signal but increasing the intensity of electrical stimulation over 10 V or 10 milliamps does not result in a decrease in the resulting beta band signal, 10 V or 10 milliamps may be determined to be the intensity of electrical stimulation that maximally suppresses the beta band signal at the position corresponding to electrode 118a because additional increases in intensity above 10 V or 10 milliamps does not result in further suppression of the beta band signal. In this example, the maximally suppressive intensity of stimulation is the intensity at which additional increases in intensity do not further suppress the beta band signals. In other examples, the maximally suppressive intensity may be the intensity of stimulation that suppresses the beta band signal to be under a threshold amount or that suppresses the beta band signal by a threshold amount.

Any combination of suitable factors or processes may be used to determine the intensity of electrical stimulation that maximally suppresses a beta band signal at a particular position. For example, as described above, the intensity of electrical stimulation may be increased at any suitable interval, for example by 0.5 V or 0.5 milliamp, and the resulting beta band signal may be sensed. The intensity of electrical stimulation may be increased as long as the resulting beta band decreases. In some examples, as described above, if an increase in intensity, for example from 10V or 10 milliamps to 10.5 or 10.5 milliamps, does not decrease the resulting beta band signal, the intensity may be increased again, for example, to 11.0 V or 11.0 milliamps, and the resulting beta band signal sensed to determine whether any decrease results. This increase in intensity following an increase that results in no decrease in the beta band signal may be repeated, for example, two or three times, to determine that an increase in intensity over 10 V or 10 milliamps does not result in a decrease in the beta band signal. Based on this determination, 10V or 10 milliamps may be determined to be the intensity that maximally suppresses the beta band signal for that position.

As another example, intensity of electrical stimulation may be increased until patient 104 exhibits improvement in symptoms that may indicate optimal suppression of the beta band signal. For example, intensity of delivered electrical stimulation may be increased at regular intervals until, in the case of patient 106 having Parkinson's disease, patient 106 is able to, for example, increase speed of intentional movement to a desired or optimal speed. For example, electrical stimulation may be delivered at increasing intensity until a desired patient response is reached and/or until a patient response is optimized such that additional increases in intensity do not result in an improved patient response. Desired patient responses may include, for example, increased speed of intentional movement, decrease in tremor or pain, improved sensory activities or acuity, reduced bradykinesia, improved sleep or other benefits. Such results may be monitored with diagnostic tools and/or manually, such as visually, by a clinician. Patient responses to incremental changes in stimulation intensity may also be monitored and used for defining the therapy target. For instance, scores assigned by a clinical observer according to a standardized rating scale such as the Unified Parkinson's Disease Rating Scale (UPDRS) based on patient evaluation and patient responses may in some examples be used for defining the therapy target.

In some examples, increases in intensity may be stopped if adverse side effects are observed or if no further suppression is achieved. For example, in the example described above, intensity of electrical stimulation may be increased at intervals of 0.5 V or 0.5 milliamp as long as the resulting beta band signal decreases and until adverse symptoms are observed. For example, decreases in the beta band signal may result for each increase in stimulation intensity from 0.5 V or 0.5 milliamp to 1.0 V or 1.0 milliamp, then from 1.0 V or 1.0 milliamp to 1.5 V or 1.5 milliamps, etc. up to 8.0 V or 8.0 milliamps with no adverse side effects observed. However, increasing the intensity another 0.5 V or milliamp interval, from 8.0 V or 8.0 milliamps to 8.5 V or 8.5 milliamps may result in a decreased beta band signal but may also result in an adverse side effect. As a result, the intensity that maximally suppresses the beta band signal may be determined to be 8.0 V or 8.0 milliamps, which is the intensity that suppresses the beta band signal the most without also causing adverse side effects. Adverse side effects may include, for example, eye twitching, facial muscle twitches, speech difficulties, visual side effects, or other problematic side effects. Such side effects may be monitored with diagnostic tools and/or manually, such as visually, by a clinician.

After the responsiveness of the beta band signal to electrical stimulation is determined for the position corresponding to 108a for a plurality of intensities of electrical stimulation, electrical stimulation may be delivered at other positions to determine the responsiveness of the beta band signal to electrical stimulation at those positions. In some examples, the first electrical stimulation to be delivered at the other positions may be determined based on the intensity determined to be suppressive at the position corresponding to 108a. For example, for the position corresponding to 108b, where the normalized local field potential was determined to be "0.9" when normalized with respect to the local field potential at the position corresponding to 108a, the first intensity of electrical stimulation to be delivered may be 0.9 times the intensity determined to maximally suppress the beta band signal at the position corresponding to 108a (10 V or 10 milliamps). For example, the first intensity to be delivered at the position corresponding to 108b may be 0.9×10 V or 10 milliamps, which is 9 V or 9 milliamps.

Sensing circuitry 206 may sense the beta band signal at the position corresponding to 118b when electrical stimulation is not delivered. The beta band signal may be, for example 9 μV. Controller 202 and/or controller 302 may control electrical stimulation circuitry 204 to deliver electrical stimulation at 9V or 9 milliamps and sensing circuitry 206 may sense the beta band signal resulting from the delivered electrical stimulation. The resulting beta band signal may be, for example, 1.5 μV, such that the delivery of the electrical stimulation reduced the sensed beta band signal from 9 μV to 1.5 μV. Electrical stimulation intensity may be increased, for example, in intervals of 0.5 V or 0.5 milliamp to determine whether increases in the intensity results in additional suppression. In some cases, additional suppression may not result from increases in intensity from the first intensity used. For example, increases to 9.5 V or 9.5 milliamps and 10.0 V or 10.0 milliamps may still result in the same sensed beta band signal of 1.5 μV. In some examples, intensity may be decreased to determine whether the first delivered electrical stimulation was of the smallest intensity that maximally suppresses the beta band signal. For example, the intensity may be decreased from 9.0 V or milliamps to 8.5 V or milliamps to determine whether the beta band signal sensed in response increases. If it does increase as the intensity is decreased, then the originally delivered intensity may be the intensity that maximally suppresses the beta band signal. If decreasing the intensity results in an increase in the beta band signal, then the originally delivered stimulation may be determined to be the intensity that maximally suppresses the beta band signal. If decreasing the intensity of electrical stimulation delivered does not result in an increase in the beta band signal, then the intensity may be decreased in intervals until the lowest intensity that does not result in an increase in the beta band signal is determined and that intensity may be determined to the be intensity that maximally suppresses the beta band signal.

For the position corresponding to 118b, as with the position corresponding to 118a, patient 106 may be monitored for desirable effects and/or for adverse side effects to help determine the intensity that maximally suppresses the beta band signal but does not result in adverse side effects and to determine responsiveness to electrical stimulation, including changes in response to changes in intensity of the electrical stimulation.

In some examples, delivered electrical stimulation at some positions may not result in a decrease in the beta band signal. For example, for each of the positions corresponding to 118c and 118d, electrical stimulation may be delivered at a plurality of intensities and the beta band signal may be sensed in response to the delivered electrical stimulation. However, the delivery of electrical stimulation at each of the plurality of intensities may be determined to not decrease the beta band signal from the beta band signal sensed when no electrical stimulation is delivered. Thus the intensity of electrical stimulation that maximally suppresses the beta band signal at those positions may be determined to be zero and the beta band signal may be determined to have no response to electrical stimulation.

Based on the responsiveness of the beta band signal to electrical stimulation at each of the positions corresponding to electrodes 108a, 108b, 108c, and 108d, controller 202 and/or controller 302 may define a therapy target. The therapy target definition may include information that may be used to select parameters for delivering therapy, forming a lesion, monitoring the size and position of source 108, monitoring the position of lead 114 with respect to source 108, and/or for any other suitable purpose according to particular needs. The information included in the therapy target definition may include, for example, the intensity of electrical stimulation that maximally suppresses the beta band signal for each of the positions. These may be, for the example described above, 10 V or milliamps for the position corresponding to 108a, 9 V or milliamps for the position corresponding to 108b, 0 V for the position corresponding to 108c, and 0 V for the position corresponding to 108d. The information may also include, for example, the sensed local field potentials at each of the positions when electrical stimulation is not delivered. The values may include, for example, the values with respect to reference value or normalized values as described above with respect to the example shown in FIG. 5. For example, the normalized values for the positions corresponding to each of 118a, 118b, 118c, and 118d, may be 1.0, 0.9, 0.7, and 0.5, respectively. Any other suitable information may also be included in the definition of the therapy target. The responsiveness of the beta band signal to electrical stimulation at each of a plurality of positions may also be included in the definition of the therapy target.

In some examples, the defined target may define a spatial extent of source 118. For example, based on the responsiveness of the beta band signals to electrical stimulation at each of the positions in the example above, controller 202 and/or controller 302 may determine that source 108 is adjacent to the positions corresponding to electrodes 118a and 118b (i.e., span the length of those positions) because electrical stimulation delivered at those positions suppresses the beta band signal sensed at those positions.

For each of the positions corresponding to 118a and 118b that are determined to be adjacent to source, controller 202 and/or controller 302 may also determine the span of source 108 in the radial direction away from the position. A width of source 108 adjacent to any particular position along lead 114 may be, for example, in the range of 0.01-50 mm, or in the range of between 0.1-10 mm, and the information obtained by the iterative process of sensing the local field potentials and beta band signals at the plurality of positions and determining the responsiveness of the beta band signals or some other biomarker of the sensed signal that indicates responsiveness to electrical stimulation for each position, may be used to determine the span and position of the source 108 with respect to the lead 114.

For example, beta band signals may be sensed along the lead 114. In sequence, as described above, or simultaneously, stimulation pulses may be delivered and titrated (with different amplitude pulses) to determine the responsiveness or sensitivity to stimulation along the length of lead 114. A large beta signal at one position along the lead may suggest that a dysfunctional tissue is near the position. The tissue may, however, be a nearby tissue that is moderately dysfunctional or a more distant tissue that is more significantly dysfunctional. Both of these conditions may result in the observed beta signal. But beta suppressive stimulation of different magnitudes can be delivered along the trajectory and may allow differentiation of an appropriate distance estimate for the dysfunctional tissue relative to the trajectory. A small stimulation may produce a small field. Suppression of the beta signal by a small stimulation may indicate a dysfunction source nearer to the trajectory. Alternatively, if the small signal does not suppress the beta signal, the dysfunction source may be estimated to be further from the trajectory.

By determining the responsiveness of the beta band signals to electrical stimulation, controller 202 and/or controller 302 may determine an extent of source 108 in a direction away from lead 114 for each of the selected positions, including positions corresponding to electrodes 118a and 118b. For example, the intensity needed to suppress a signal at a given position may indicate a larger extent of source 108 away from lead 114. For example, the larger the intensity needed to suppress the signal sensed at a particular position, the further that source 108 may extend away from lead 114. For example, a larger intensity may be needed at a position corresponding to electrode 118a than at the position corresponding to electrode 118b because source 108 extends further from lead 114 at the position corresponding to electrode 118a.

In combination with one or more electrical signals sensed when electrical stimulation is not delivered the responsiveness of the beta band signals to electrical stimulation may be used to define a spatial extent of source 108. For example, the responsiveness of the beta band signals to electrical stimulation may help to differentiate between a close and small source and a large and far away source that may each result in a similar sensed signal when electrical stimulation is not delivered. Using this information, controller 202 and/or controller 302 may define a therapy target that includes, for example, a spatial mapping of source 108.

In some examples, controller 202 and/or controller 302 may record a first intensity at which suppression of the beta band signal first occurs and a second intensity at which maximal suppression is achieved (additional increases in intensity does not further suppress the beta band signal or the beta band signal is suppressed by a predetermined threshold amount or to be under a predetermined threshold amount). The first intensity may be indicative of a near edge of the source and the second intensity may be indicative of the far edge of the source.

This iterative process of stimulation and sensing may be performed for each position within brain 106 determined to be of interest. For example, in the example of FIGS. 4A and 6A, this process may be performed for the positions corresponding to each of electrode 118a, 118b, 118c, and 118c. Suppressive stimulation field 602a is representative of a stimulation field at the position corresponding to electrode 118a that is a function of an intensity of the stimulation that maximally suppresses beta band signals sensed at the position by maximally reducing the power or amplitude of the beta band signal. In some examples, other indications of suppression or enhancement such as, for example, patient responses, including movements, that indicate suppression of an undesired signal or enhancement of a desired signal, may be used to indicate that the responsiveness of the beta band signal to electrical stimulation. Suppressive stimulation field 602b is representative of stimulation field at the position corresponding to electrode 118a that is a function of an intensity of stimulation that substantially suppresses beta band signals sensed at the position. Examples of intensities of electrical stimulation that may be sufficient to suppress beta band signals may be, for example, in the range of approximately 1.5 volts to 5 volts or 1.5 milliamps to 5 milliamps. For some applications, higher voltages or current may be needed to maximally suppress the desired signal, for example 5 to 10 volts or 5 to 20 milliamps. As described above, in the illustrated example, no intensity of electrical stimulation may result in suppression of the beta band signal at the positions corresponding to 118c and 118d such that no suppressive stimulation field is shown for those positions.

Based on the responsiveness of the beta band signals to electrical stimulation and the electrical signals sensed when electrical stimulation was not delivered, controller 202 and/or controller 302 may define a therapy target corresponding to a spatial extent of source 108. For example, as described above, the responsiveness of the beta band signals to electrical stimulation at a particular position may indicate the extent of the source 108 in a radial direction away from the position, with a larger intensity needed to suppress the signal indicating a further extent of the source 108 away from the lead 114, and the electrical signal sensed when electrical stimulation is not delivered may further indicate the span of source, with a source 108 of a particular size having a larger sensed signal when closer to the position on lead 114. In some examples, controller 202 and/or controller 302 may control delivery of therapy to brain 106 of patient 104 based on the therapy target definition. For example, based on the therapy target definition corresponding to a spatial definition of source 108, controller 202 and/or controller 302 may control delivery of therapy including electrical stimulation to treat source 108, electrical stimulation to create a lesion corresponding to the spatial extent of source 108, and/or any other suitable therapy. Controller 202 and/or controller 302 may control parameters such as stimulation amplitude, frequency, and/or pulse width in order to adjust intensity to tailor therapy to source 108 based on the therapy target definition.

In some examples, the stimulation intensity at each position that maximally suppresses beta activity can be used directly for a final clinical setting in which therapy is delivered by delivering corresponding electrical stimulation at the intensity for each corresponding position. In other examples, a spatial mapping of the source may be stored based on the maximally suppressive intensities and the mapping may be used to select therapy parameters.

The combination of the sensed local field potential amplitude when electrical stimulation is not delivered and the response of a sensed signal to electrical stimulation at one or more positions may be used to spatially map the source 108. For example, measurements for local field potential amplitudes may be in the range of approximately 0.02 to 10 µV. As an example, a point source for highly dysfunctional tissues that are a small distance from the measurement electrode may produce a high amplitude signal without stimulation. As electrical stimulation amplitude is increased (for example from 0 to 10 V) the electrical field may extend away from the stimulation lead from approximately 0 mm to −8 mm. The relationship between the stimulation amplitude and the local field potential measurement may reveal the size or volume of the dysfunctional tissue. For example a steady constant but small (for example slope=−(0.05−0.15)µV/V) decrease with stimulation amplitude increase may suggest that dysfunction is spread throughout or more evenly across the tissue. Conversely a rapid and large decrease with stimulation amplitude (for example slope=−0.2−3 µV/V) beginning at a specific amplitude may reveal a proximal margin of the dysfunctional tissue has been identified by the stimulation. In this manner, combinations of stimulation and sensing can be used to identify basic tissue dysfunction states, approximate locations and volume within the brain tissue near the site. Additionally and in a similar manner, changes in patient responses, such as changes in disorder symptoms described above, as a result of changes in stimulation intensity, may be used in addition or alternatively to define the spatial extent of the therapy target.

Although the illustrated examples describe delivering electrical stimulation to suppress a sensed signal characteristic, electrical stimulation may be delivered, in some example applications, to further enhance, rather than suppress, a sensed signal characteristic. For example, controller 202 and/or controller 302 may control electrical stimulation circuitry 204 to deliver electrical stimulation and sensing circuitry 206 may sense electrical signals resulting from the delivered stimulation to identify the intensities of electrical stimulation that enhance the sensed signal characteristic. A therapy target may be defined based on the responsiveness of the sensed signal characteristic to electrical stimulation for each of a plurality of positions and the therapy target definition may be used to select therapy parameters and to deliver therapy, form a lesion, monitor source 108 and/or the position of lead 114 and electrodes 118 with respect to source 108, and/or for any other suitable purpose.

During delivery of electrical stimulation for definition of the target, each selected electrode, electrode segment, and/or group of electrodes, such as 118a, 118b, 118c, and 118d in this example, may deliver electrical stimulation individually in a unipolar manner with another electrode in IMD housing 112, or in a bipolar manner with another electrode on lead 114. During delivery of therapy, delivery of therapy may be via all of the selected electrodes, such as electrodes 118a, 118c, 118c, and 118d, whether simultaneously or at least in a temporally overlapping manner, or by delivery via different electrodes corresponding to particular time slots. Therapy can be delivered using unipolar or bipolar stimulation.

FIG. 6B illustrates an example including lead 114 with electrodes 118 adjacent to spherical source 408. As described with reference to FIGS. 4B and 5, local field potentials may be sensed at each of the positions corresponding to electrodes 118a, 118b, 118c, and 118d. Based on the sensed local field potentials, as shown in FIG. 5, controller 202 and/or controller 302 may determine that the position corresponding to electrode 118a has the largest sensed local field potential when electrical stimulation is not delivered. Thus, controller 202 and/or controller 302 may control electrical stimulation circuitry 204 to first deliver electrical stimulation at a position corresponding to electrode 118a. For example, controller 202 and/or controller 302 may control electrical stimulation circuitry 204 to deliver electrical stimulation at the position via electrode 118a. In other suitable examples, electrical stimulation may be delivered to positions corresponding to each of 118a, 118b, 118c, and 118d in any suitable order and/or simultaneously. In some examples, electrical stimulation may only be delivered at selected positions based on the local field potential sensed at each of the positions when electrical stimulation is not delivered.

As described with reference to FIG. 6A, an iterative process of delivering electrical stimulation at a plurality of intensities, for example, at a plurality of increasing intensities, and sensing electrical signals in response to the delivered electrical stimulation, may be performed to determine the responsiveness of the beta band signals to electrical stimulation. The intensity of suppressive stimulation may be represented by suppressive stimulation field 604, corresponding to an electrical stimulation that substantially suppresses beta band signals sensed at the position corresponding to electrode 118a or otherwise suppressing beta band signals to satisfy a predetermined criteria. The responsiveness of the beta band signals to electrical stimulation as determined by this process, may be used by controller 202 to define a therapy target corresponding to source 408. In some examples, defining the therapy target may be further based on the local field potentials sensed before delivery of electrical stimulation as described with reference to FIGS. 4B and 5. In some examples, the therapy target definition may correspond to a spatial definition of source 408. In some examples, the therapy target definition may be information indicating the responsiveness of the beta band signals to electrical stimulation at one or more positions, a responsiveness of some other biomarker to electrical stimulation, local field potentials sensed when electrical stimulation is not delivered, and/or parameters or other information that are a function of the responsiveness of the beta band or other biomarker signals to electrical stimulation at one or more positions and/or local field potentials. Examples of other biomarker signals may include time-domain characteristics of a sensed signal, such as an instantaneous or time-averaged signal amplitude exceeding or dropping below a high or low threshold, respectively. Other examples may include a particular waveform morphology as may be determined based on template matching, or any other sensed characteristic in the time or frequency domain that is indicative of responsiveness (e.g., responsiveness of affected tissue) to stimulation. In some example, the defined target may be used for determining parameters for therapy delivery, whether or not the therapy target definition is indicative of a spatial extent of source 108.

In some examples, the iterative process of delivering electrical stimulation and sensing electrical signals to determine the responsiveness of the beta band signals to electrical stimulation may also be performed for other positions along lead and may, in some examples, not result in suppression of the beta band signal such that no responsiveness of the beta band signals to electrical stimulation is determined.

FIG. 6C illustrates an example including lead 114 with electrodes 118 adjacent to source 608. A similar process, as described with reference to FIGS. 6A-6B may be performed to sense local field potentials at each of positions corresponding to electrodes 118a, 118b, 118c, and 118d of lead 114 (in some examples, select positions based on the sensed local field potentials), and iteratively deliver stimulation and sense beta band signals at the plurality of (selected) positions to determine a therapy target definition. Suppressive stimulation fields 606a and 606b may correspond to stimulations at intensities sufficient to suppress beta band signals sensed at each of the selected positions. Suppressive stimulation fields 606a and 606b may be substantially similar to suppressive stimulation fields 602a and 602b, respectively, of FIG. 6A for triangular source 108. However, the responsiveness of the beta band signals to electrical stimulation for each case may be used, in combination with sensed local field potentials for each of the selected positions, to determine information representative of a therapy target that corresponds to the spatial extent of each of source 108 and source 608. The representative information may, for example, indicate positions at which a sensed local field potential is over a threshold amount, a function of the sensed local field potentials at one or more positions, intensities or functions of intensities for suppressive stimulation at one or positions, and/or other information indicating the responsiveness of the beta band signals to electrical stimulation at one or more positions.

For example, although suppressive stimulation field 606a may be similar to suppressive stimulation field 602a, each corresponding to a position corresponding to electrode 118a, such that the intensity of the suppressive stimulation at each of those positions are similar, a local field potential sensed at the position may be lower in the example of source 608 than in the example of source 108 due to the greater distance between the portion of source 608 adjacent to lead 114 and lead 114 than the distance between the portion of source 108 adjacent to lead 114 and lead 114. However, both the sensed local field potentials at each of the positions corresponding to electrodes 118a and 118b and the determination of the intensity of electrical stimulation sufficient to suppress beta band signals at those positions may be used together by controller 202 to define a therapy target that corresponds to a spatial extent of a source and to thus differentiate between these different source shapes and locations. Additionally, the responsiveness of the beta band signals to electrical stimulation at the position corresponding to electrode 118a may be used to determine the position of the source adjacent to the position, as described in further detail above with reference to FIG. 6A.

More generally, a source that is close to a position on lead 114 may result in a sensed local field potential that is larger than if the source were further away. A source that extends far away from the position on lead 114 may require a larger intensity for suppression than if the source did not extend as far. Thus, for a given position, a small sensed local field potential and a large intensity of stimulation needed for suppression may indicate that the source is far from the position on lead 114 and extends out in the radial direction from lead 114 by a small amount, i.e., the portion corresponding to that position is close and small. A large sensed local field potential and a large intensity of stimulation needed for suppression may indicate that the source is close to the position of lead 114 and extends out in the radial direction from lead 114 by a large amount, i.e., the portion corresponding to that position is close and large. Additionally or alternatively, the responsiveness of the beta band signals to electrical stimulation at one or more positions may be used to determine the boundaries of source 108 within brain 106. Using these determinations for multiple positions along and/or about the longitudinal axis of lead 114, i.e., at different longitudinal positions along the length of the lead and/or at different angular positions around the circumference of the lead, may allow for constructing a 3-dimensional mapping of the shape of the source 108 within brain 106.

Figure 7A:
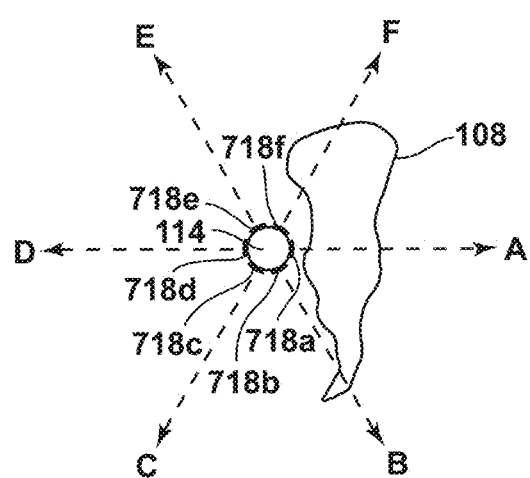
FIGS. 7A and 7B are diagrams illustrating cross-sectional views of example electrode configurations for delivering electrical stimulation at a plurality of different intensities at each of a plurality of different positions within a brain of a patient and sensing electrical signals at each of the different positions in response to the electrical stimulation taken along lines 7A-7A and 7B-7B of FIG. 6A, respectively.
Figure 7B:
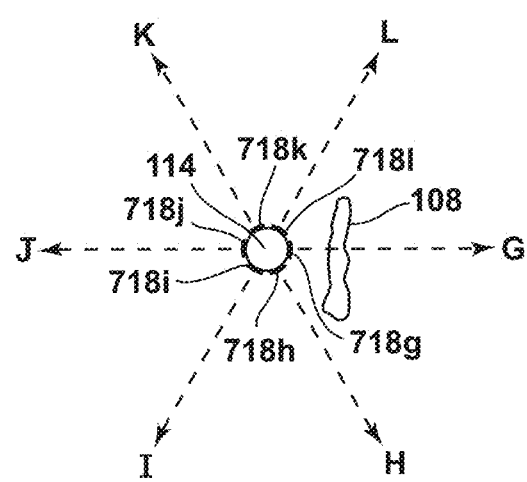

FIGS. 7A and 7B are diagrams illustrating cross-sectional views of example electrode configurations for delivering electrical stimulation at a plurality of different intensities at each of a plurality of different positions within brain 106 of patient 104 and sensing electrical signals at each of the different positions in response to the electrical stimulation taken along lines 7A-7A and 7B-7B of FIG. 6A, respectively.

FIG. 7A includes a cross-sectional view of lead 114, electrode 118a, and source 108 taken along the line 7A-7A in FIG. 6A. As described above with reference to FIGS. 1A and 1B, one or more of electrodes 118 may include segmented electrodes or other types of electrodes that may allow for delivery of stimulation and/or sensing in any suitable circumferential position about lead 114. For example, electrode 118a may include a plurality of segments 718a-718f extending around different circumferential portions of the lead, and each corresponding to a different circumferential position A-F. As another example, electrode 118a may include a segmented electrode that extends around less than the entire circumference of the lead and that allows for stimulation and/or sensing in one particular circumferential direction about lead 114 at a time (has partial ring contact) and may be rotated, for example by motor 122 of FIG. 1A during implantation, to deliver stimulation and/or sense at each of the circumferential positions A-F.

As described with reference to FIGS. 5A-5C, local field potentials may be sensed at a plurality of positions within brain 106 and, in the illustrated example of FIG. 7A, they may be sensed at each of the circumferential positions A-F, by segments 718a-718f of electrode 118a corresponding to different circumferential positions A-F and/or by rotation of electrode 118a.

In some examples, selected positions may be determined to be of interest (for further analysis including delivery of electrical stimulation and sensing of electrical signals in response to the delivered electrical stimulation) based on the sensed local field potentials. In other examples, positions may be of interest based on determining that electrical stimulation suppresses an electrical signal at that position. For example, circumferential positions A, B, and F may be of interest while circumferential positions C-E may not be of interest based on the local field potentials sensed or the suppression of electrical signals by electrical stimulation for each position A-F. In some examples, controller 202 and/or controller 302 may be configured to control the rotation of lead 114 and/or the sensing of segments 718a-718f of electrode 118a about lead 114 to determine circumferential selected positions by sensing and/or delivering stimulation at predetermined intervals about lead 114, in either direction about lead 114 until a particular position is not of interest (because the sensed local field potential sensed at that position is under a threshold amount or because a sensed signal at that position is not suppressed by delivery of electrical stimulation). For example, controller 202 and/or controller 302 may be configured to control sensing of local field potential and/or delivery of electrical stimulation at circumferential position A, then F, then E. When the local field potential is under a threshold amount or a sensed signal is not suppressed in response to electrical stimulation at position E, such that position E is determined not to be of interest, controller 202 and/or controller 302 may control sensing and/or delivering electrical stimulation at circumferential position B, then C, until, again a position, in this example position C, is determined to not be of interest. In this way, controller 202 and/or controller 302 may limit unnecessary sensing and/or delivery of electrical stimulation at circumferential positions about lead 114, such as, in this example, circumferential position C.

The iterative process of delivering stimulation at different intensities and sensing beta band signals until the beta band signals are sufficiently suppressed may be performed for each of positions A, B, and F. This process may also be performed, for example, at position E or any other suitable position. Controller 202 and/or controller 302 may then further define a therapy target corresponding to source 108 based on the sensed local field potentials and the responsiveness of the beta band signals to electrical stimulation for each of the circumferential positions. For example, the local field potential and the responsiveness of the beta band signals to electrical stimulation for circumferential position A may help to define a therapy target indicative of the spatial extent of source 108 in the direction of circumferential position A, which may be different than that determined for circumferential positions B and F. For example, for delivery of electrical stimulation therapy, a given electrode may have an intensity that is selected as a function of the intensity that achieved suppression of the beta band signal by a desired degree. Additionally, the local field potentials sensed and the responsiveness of the beta band signals to electrical stimulation for each of the circumferential positions A, B, and F may help to further define a therapy target that may, in some cases, represent a spatial extent of source 108. Positions such as position C may be determined to not be adjacent to the source because delivery of electrical stimulation at that position does not result in suppression of a sensed electrical signal at that position.

Although electrode segments 718a-718f and 718g-718l are described as corresponding to axial positions corresponding to electrodes 118a and 118b, any suitable number of electrode segments may be included on lead 114 at any suitable axial and/or circumferential positions. For example, additional electrode segments may be included at axial positions corresponding to electrodes 118c and 118d.

For selected axial positions, based on sensed local field potentials at one or more axial positions, this process of sensing local field potentials and/or determining the responsiveness of the beta band signals to electrical stimulation for any number of suitable circumferential positions may be performed, for example, using different segmented electrodes and/or by rotation of lead 114.

FIG. 7B includes a cross-sectional view of lead 114, electrode 118b with electrode segments 718g-718l, and source 108 taken along the line 7B-7B in FIG. 6A. As described with reference to FIG. 7A, local field potentials may be sensed and/or electrical stimulation may be delivered at each of circumferential positions G-L. In some examples, position L may be determined to be of interest because delivery of electrical stimulation results in suppression of a sensed signal at that position. Using the sensed local field potentials and the responsiveness of the beta band signals to electrical stimulation for each of the selected circumferential positions for selected positions along lead corresponding to electrodes 118a and 118b, a therapy target may be defined by controller 202 that corresponds to a 3-dimensional spatial extent of source 108. In some examples, the therapy target definition may not necessarily correspond to a 3-dimensional spatial extent of source 108 but may be used to derive therapy parameters for therapy of source 108. For example, one of more treatment parameters may be a function of the responsiveness of the beta band signals to electrical stimulation and/or the sensed local field potentials for the axial and/or circumferential positions.

As described in the previous examples, signals sensed when electrical stimulation is not delivered, as well as the responsiveness of the beta band signal to changes in electrical stimulation may be used to determine a mapping of the source. This process of sensing and then delivering while sensing may be performed at multiple axial positions along the lead for one circumferential position to create a 2-dimensional mapping of the source in the plane of the circumferential direction. Using segmented electrodes to perform this process for multiple circumferential directions may allow for producing multiple 2-dimensional mappings, one for each circumferential position, which may be combined to perform a 3-dimensional mapping of the source.

In some examples, the 2-dimensional or 3-dimensional mappings may be defined by the local field potentials sensed when electrical stimulation is not delivered and/or one or more intensity levels of electrical stimulation delivered and the response of the beta band signals to the stimulation signals at the corresponding intensities at each electrode to spatially define the source. In other examples, measurements of local field potentials sensed when electrical stimulation is not delivered and/or one or more intensity levels of electrical stimulation delivered and the response of the beta band signals to the stimulation signals at the corresponding intensities at each electrode may be converted to spatial coordinates, shapes, sizes, etc. that may be stored and used to select parameters, monitor changes, etc. In this manner, defining the therapy target (as a 2D or 3D mapping or otherwise) may comprise defining parameters for delivering therapy, including, for example, selecting electrodes for delivery of electrical stimulation and/or selecting intensities of electrical stimulation delivered by the selected electrodes. For example, selected electrodes and selected intensities may define the therapy target and directly form parameters for delivery of electrical stimulation. In other examples, the therapy target may be defined and then the stimulation parameters may be selected based on the therapy target definition such that the parameters for delivering stimulation therapy are different from the parameters that define the therapy target.

Figure 8A:
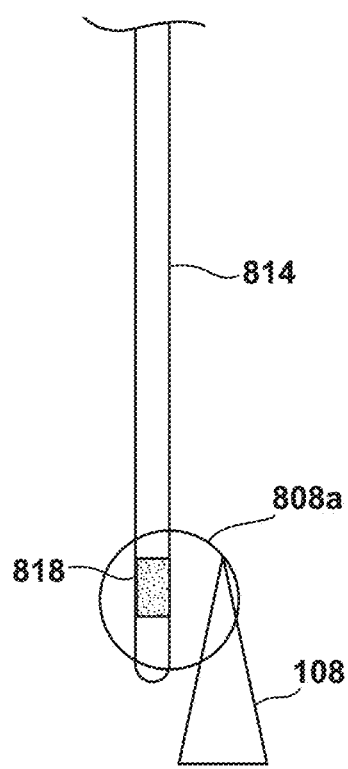
FIGS. 8A and 8B are diagrams illustrating another example electrode configuration for delivering electrical stimulation at a plurality of different intensities at each of a plurality of different positions within a brain of a patient and sensing electrical signals at each of the different positions in response to the electrical stimulation.
Figure 8B:
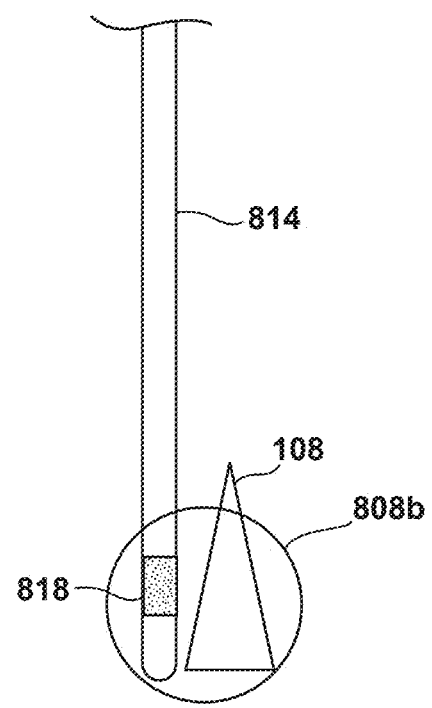

FIGS. 8A and 8B are diagrams illustrating another example electrode configuration for delivering electrical stimulation at a plurality of different intensities at each of a plurality of different positions within brain 106 of patient 104 and sensing electrical signals at each of the different positions in response to the electrical stimulation.

Lead 814 may be an example lead similar to lead 114 of FIGS. 1A-6B. Electrode 818 may be an example electrode similar to each of electrodes 118 of FIGS. 1A-7B and/or may include a group of electrodes corresponding to one or more axial positions along the length of lead 814. Lead 814 and electrode 818 may be controlled by controller 202 to perform the process described with reference to FIGS. 4A-8B. Instead of using different electrodes along a lead to sense local field potentials and perform the iterative process to determine the responsiveness of the beta band signals to electrical stimulation, the same electrode or group of electrodes 818 may be used while lead 814 is positioned within brain 106. For example, motor 122 may be a step-wise motor for advancing lead 814 within brain 106. As lead 818 advances within brain 106, electrode 818 may sense local field potentials, including at several positions axial along the longitudinal axis of lead 818. Lead 818 may also sense local field potentials at several circumferential positions using segments of a segmented electrode and/or rotation of lead 118 about longitudinal axis of lead 818.

The iterative process as described with reference to FIGS. 6A-7B may be performed to determine the responsiveness of the beta band signals to electrical stimulation for each of the selected positions. In some examples, the iterative process may be performed only for positions at which the sensed local field potentials are over a threshold amount. In other examples, the iterative process may be performed at all positions. In other examples, the iterative process may be performed for each position until a boundary of the source is determined at which electrical stimulation does not result in suppression of a sensed signal when the electrical stimulation is delivered, at which point positions beyond the boundary may not be used for delivery of electrical stimulation and sensing of a change in a signal in response to the stimulation, as described above. Based on the sensed local field potentials and the responsiveness of the beta band signals to electrical stimulation for one or more positions, controller 202 and/or controller 302 may define a therapy target corresponding to a spatial extent of source 108. The process of sensing local field potentials and determining the responsiveness of the beta band signals to electrical stimulation may be performed in any suitable order. For example, lead 814 may be placed as shown in FIG. 8A and local field potentials may be sensed at one circumferential position about lead 814 and the responsiveness of the beta band signals to electrical stimulation may be determined at that position before rotation and performing these steps for another circumferential position or advancing lead 814. As another example, local field potentials may be sensed for each of multiple circumferential positions about lead 814, lead 814 may be advanced (lowering lead 814 to the target brain tissue), and local field potentials may be sensed at circumferential positions about lead 814 until all selected positions, whether circumferential or along lead 814, are determined, and then the responsiveness of the beta band signals to electrical stimulation may be determined for each of the selected positions. Any other suitable order of steps may be formed according to particular needs. In some examples, suppressive electrical stimulation may be determined in a sequence as a function of the sensed local field potentials. For example, suppressive electrical stimulation may be determined first at the position with the highest sensed local field potential, then at the position with the second highest local field potential, and so on.

Lead 814, lead 114, or any suitable lead may be used to define a therapy target and/or to deliver therapy. A lead may be a chronic lead used to define the therapy target and for chronic treatment within brain 106 or may be a test lead for defining the therapy target and may be removed before therapy is delivered based on the defined target using another device. Additionally, a lead may be used to define a therapy target, deliver short-term therapy based on the therapy target definition, and subsequently removed from brain 106.

Figure 9:
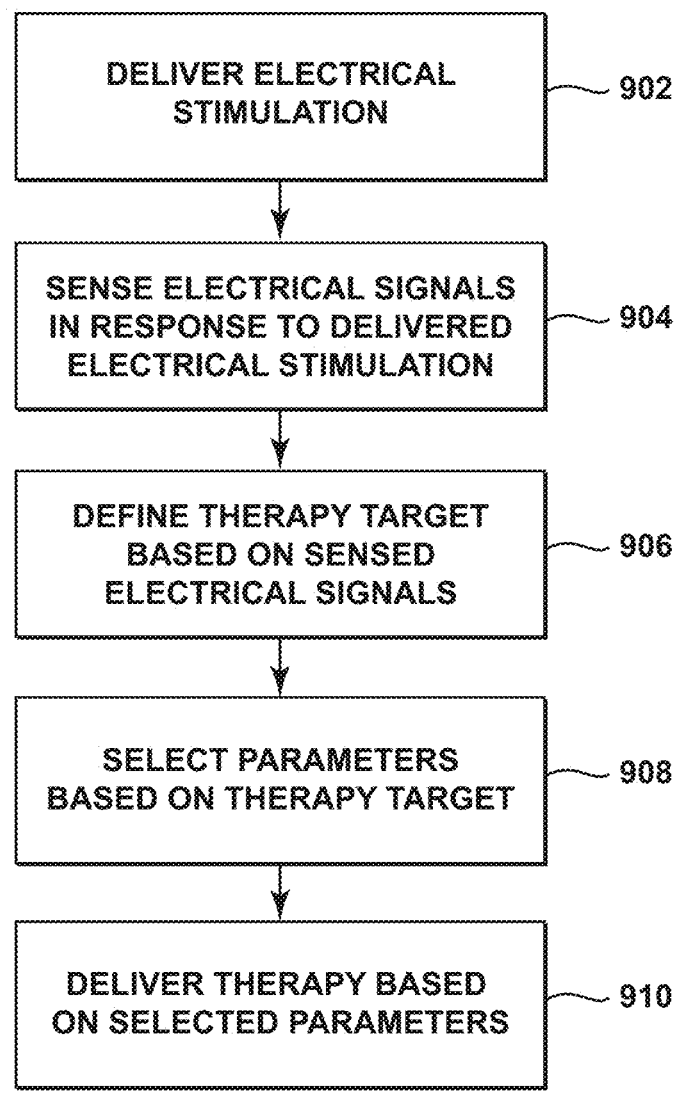
FIG. 9 is a flow diagram of an example technique for defining a therapy target, selecting therapy parameters based on the therapy target definition, and delivering therapy to a brain of a patient based on the selected parameters.

FIG. 9 is a flow diagram of an example technique for defining a therapy target, selecting therapy parameters based on the therapy target definition, and delivering therapy to brain 106 of patient 104 based on the selected parameters.

Electrical stimulation may be delivered at a plurality of different intensities at each of a plurality of different positions within brain 106 of patient 104 via selected combinations of electrodes 108 (902). For example, controller 202 and/or controller 302 may control electrical stimulation circuitry 204 to deliver electrical stimulation at a plurality of different intensities at each of a plurality of different positions within brain 106 of patient 104 via selected combinations of electrodes 108. For example, as described with respect to FIGS. 4A-8B, controller 202 and/or controller 302 may control electrical stimulation circuitry 204 to deliver electrical stimulation at a plurality of selected positions including, for example, a plurality of axial positions along a length of lead 114 and/or a plurality of circumferential positions about a circumference of lead 114. Electrical stimulation may be delivered at a plurality of intensities including, for example, at progressively larger intensities to identify the responsiveness of the beta band signals to electrical stimulation at each position.

Electrical signals may be sensed at each of the plurality of different positions within the brain 106 of the patient 104 in response to the electrical stimulation delivered at each of the plurality of different positions at the plurality of different intensities (904). For example, sensing circuitry 206 may sense electrical signals at each of the different positions within brain 106 of patient 104 in response to the electrical stimulation delivered at each of the different intensities. For example, as described with reference to FIGS. 4A-8B, sensing circuitry 206 may sense beta band signals at each of the axial and/or circumferential positions to determine the responsiveness of the beta band signals to electrical stimulation for each position. For example, sensing circuitry 206 may sense beta band signals as each of the progressively larger stimulation intensities are delivered to sense beta band signals corresponding to each of the intensities of electrical stimulation delivered for each of the positions. In some examples, sensing circuitry 206 may sense beta band signals as each of the progressively larger stimulation intensities are delivered and controller 202 and/or controller 302 may identify the first intensity of electrical stimulation to substantially suppress beta band signals by a predetermined amount by, for example, limiting beta band signals more than other intensities. In some examples, at some positions, delivery of electrical stimulation may not result in suppression of electrical stimulation such that no suppressive intensity is determined for that position. Controller 202 and/or controller 302 may further determine the responsiveness of the beta band signals to electrical stimulation at one or more positions.

In some examples, sensing the electrical signals comprises sensing the electrical signals at each of the different positions via a plurality of electrodes, such as electrodes 118a and 118b, implanted proximate to respective positions of the plurality of different positions, and wherein the plurality of different positions comprise combinations of a plurality of axial positions along a length of lead 114 and a plurality of circumferential positions about a circumference of lead 114.

A therapy target may be defined based on the sensed electrical signals to provide a therapy target definition (906). For example, controller 202 and/or controller 302 may define a therapy target definition based on the sensed electrical signals. For example, based on the delivered electrical stimulation and the sensed beta band signals in response to the delivered electrical stimulation, controller 202 and/or controller 302 may define a therapy target corresponding to the source of beta oscillation, such as, for example, source 108, that may correspond to a spatial extent of source 108. Controller 202 and/or controller 302 may do so, for example, at least in part by determining the responsiveness of the beta band signals to electrical stimulation. For example, as progressively larger stimulation intensities are delivered for a particular position and beta band signals are sensed in response to each progressively larger stimulation intensity, controller 202 and/or controller 302 may identify the responsiveness of the beta band signals to electrical stimulation. Controller 202 and/or controller 302 may further compare sensed beta band signals for each intensity to those of other intensities and determine the intensity that suppresses the beta band signal the most or just as well as other intensities. The therapy target definition may be further defined based on local field potentials sensed at each position when electrical stimulation is not delivered.

In some examples, defining the therapy target definition may comprise defining parameters, including, for example, selecting electrodes and/or intensities for delivering electrical stimulation for therapy. In such examples, the defined parameters may be representative of a therapy target definition that is a function of a spatial extent of the source. For example, selected electrodes and selected intensities may define the therapy target and directly form parameters for delivery of electrical stimulation. In other examples, the therapy target may be defined and then the stimulation parameters may be selected based on the therapy target definition.

In some examples, the therapy target definition may not indicate a spatial extent of source 108, although it may include information that may be used to indicate a spatial extent of source 108. For example, the therapy target definition may include information, such as the responsiveness of the beta band signals to electrical stimulation at one or more positions, which may be used by controller 202, programmer 120, or any other suitable device to create a spatial mapping of source 108. In other examples, the therapy target definition may indicate the spatial mapping of source 108.

In some examples, controller 202 and/or controller 302 may convert the therapy target definition to a graphical representation of the spatial extent of source 108 for display to a user. The graphical representation may be displayed, for example, via user interface 304 for use by a user during programming of IMD 110 and/or at any other suitable time, including during implantation, testing, and/or after implantation of lead 114, according to particular needs. The graphical representation may be used by a user to help select therapy programs and/or therapy parameters and/or to monitor source 108, including changes to source 108, and/or a position of lead 114 and/or electrodes with respect to source 108.

One or more parameters of therapy to be delivered to a brain of a patient may be selected based on the therapy target definition (908). For example, controller 202 and/or controller 302 may select one or more parameters of therapy to be delivered to brain 106 of patient 104 based on the therapy target definition. For example, controller 202 and/programmer 120 may select therapeutic electrical stimulation parameters based the therapy target definition. For example, controller 202 and/or controller 302 may select intensities for delivering electrical stimulation that are equal to or otherwise derived from the intensities determined to suppress beta band signals and/or otherwise based on the responsiveness of the beta band signals to electrical stimulation at one or more positions, as determined to define the therapy target. As another example, controller 202 and/or controller 302 may select positions and/or specific electrodes, electrode segments, and/or groups of electrodes for delivering therapeutic electrical stimulation.

The therapy target definition may include information indicating selected positions and the responsiveness of the beta band signals to electrical stimulation at each of those positions. This information may allow for selecting parameters that may include intensities that may be delivered for each of the positions that may substantially suppress beta band signals at those positions and may, for example, suppress other unwanted symptoms related to a corresponding source, such as source 108, of beta oscillations. In some examples, a selected parameter may include an intensity for a given position that may be different than an intensity identified by the therapy target definition to substantially suppress beta band signals. For example, intensities determined to substantially suppress beta band signals, as indicated in the therapy target definition, may be used to formulate a therapy program that may include applying intensities that are different than the suppressive intensities but are based on the suppressive intensities. For example, the therapy program may include delivering electrical stimulation at intensities that are a function of the determined intensities of suppressive stimulation and/or otherwise based on the responsiveness of the beta band signals to electrical stimulation at one or more positions.

As one example, a therapy target definition may indicate a first suppressive intensity of electrical stimulation corresponding to a first position, a second suppressive intensity of electrical stimulation corresponding to a second position, and a third suppressive intensity of electrical stimulation corresponding to a third position. Selecting therapy parameters may include selecting one or more amplitudes, frequencies, and/or pulse widths as functions of the first intensity, the second intensity, and/or the third intensity. The selected therapy parameters may be chosen to target the source 108 based on the example therapy target definition. In such an example, defining the therapy target may or may not include constructing a mapping of the source 108 but the parameters may still be selected to target the spatial extent of source 108 based on the responsiveness of the beta band signals to electrical stimulation at the corresponding positions in the therapy target definition.

In other examples, a mapping of the spatial extent of source 108, as determined when defining the therapy target, may be used to select therapy parameters to target the source 108 based on the mapping. In some examples, the selected parameters may be based on the mapping and/or other information, such as suppressive intensities and/or the responsiveness of the beta band signals to electrical stimulation at one or more positions, included in the therapy target definition.

As another example, controller 202 and/or controller 302 may select parameters for forming a lesion based on the therapy target definition. For example, as discussed above, the therapy target definition may indicate a spatial mapping of source 108 and controller 202 and/or controller 302 may select parameters for forming a lesion in a region of brain 108 corresponding to all or a portion of source 108 based on the spatial mapping. For example, therapy parameters (e.g., stimulation intensity and stimulation pulse width) that had maximally suppressed the beta band signals during the spatial mapping can be used to estimate the volume of tissue that is affected by the stimulation field. The particular lesion therapy parameters may be titrated such that the lesion size is targeted to substantially match the volume of tissue estimated by the spatial mapping process. Delivery of the lesion therapy may be performed through the same lead and electrodes used during the spatial mapping process. Alternatively, the lead used during the spatial mapping process may be removed, and a second lead placed at substantially the same location as the spatial mapping lead may be used to deliver the lesion therapy at the appropriate location(s).

As another example, controller 202 and/or controller 302 may select parameters for monitoring changes to source 108 and/or movement of lead 114 or electrodes with respect to source 108. For example, controller 202 and/or controller 302 may select parameters for monitoring a position of source 108 with respect to lead 114 and/or electrodes based on the therapy target definition.

Any suitable parameters may be selected based on the therapy target definition. For example, appropriate electrodes or groups of electrodes may be selected for delivery of therapy based on the therapy target definition. As another example, voltage or current amplitude, frequency, and/or pulse width of electrical stimulation pulses may be selected for delivery of therapy based on the therapy target definition. As additional examples, any suitable parameters for plasticity inductions and/or drug infusions may be selected based on the therapy target definition.

In some examples, a user may select any suitable therapy parameters based on the therapy target definition. For example, a user may view a graphical or other representation of the therapy target definition via user interface 304 and may input information indicating selection of one or more therapy parameters based on the therapy target definition.

In some examples, defining the therapy target may comprise defining parameters, including, for example, selecting electrodes and/or intensities for delivering electrical stimulation for therapy, such that a separate step of selecting therapy parameters based on the therapy target definition may not be necessary. In some examples, a separate step of selecting therapy parameters may be performed to select parameters that are some function of the parameters selected during definition of the therapy target.

Therapy may be delivered to brain 106 of patient 104 based on the selected parameters (910). For example, in some examples, controller 202 and/or controller 302 may control electrical stimulation circuitry 204 to deliver the therapy to the brain 106 of the patient 104 based on the selected parameters.

For example, controller 202 and/or controller 302 may control delivery of electrical stimulation for suppression of beta band signals based on the selected parameters. In other examples, controller 202 and/or controller 302 may control delivery of electrical current, heat, cold, or chemical material for formation of a lesion, or for any other suitable therapy, according to particular needs and based on the selected parameters. The selected parameters may facilitate efficacy in delivery of therapy. Controller 202 and/or controller 302 may also use the selected parameters to monitor changes to source 108 and/or movement of lead 114 and/or electrodes with respect to source 108. For example, controller 202 and/or controller 302 may periodically define a therapy target to determine any significant changes to the therapy target definition, as may be indicated by the selected parameters, and changes may indicate changes to source 108 and/or movement of lead 114 with respect to source 108. Observed changes may be used to adjust or change treatment accordingly.

Delivering therapy may include delivering electrical stimulation at the selected positions at the corresponding intensities determined to be suppressive at those positions. In other examples, delivering therapy may include delivering electrical stimulation at positions and intensities that are a function of the selected positions and/or the responsiveness of the beta band signals to electrical stimulation at one or more positions, respectively. For example, positions for delivery of therapy and/or corresponding intensities for electrical stimulation for therapy delivery may be based on the determined selected positions and the determined suppressive stimulation intensities and may or may not be equivalent to those positions and intensities. Delivering therapy may, for example, suppress beta band signals corresponding to those positions and/or may suppress unwanted symptoms in patient 104. As another example, delivering therapy may include performing plasticity inductions and/or drug infusions using parameters selected based on the therapy target definition.

Figure 10:
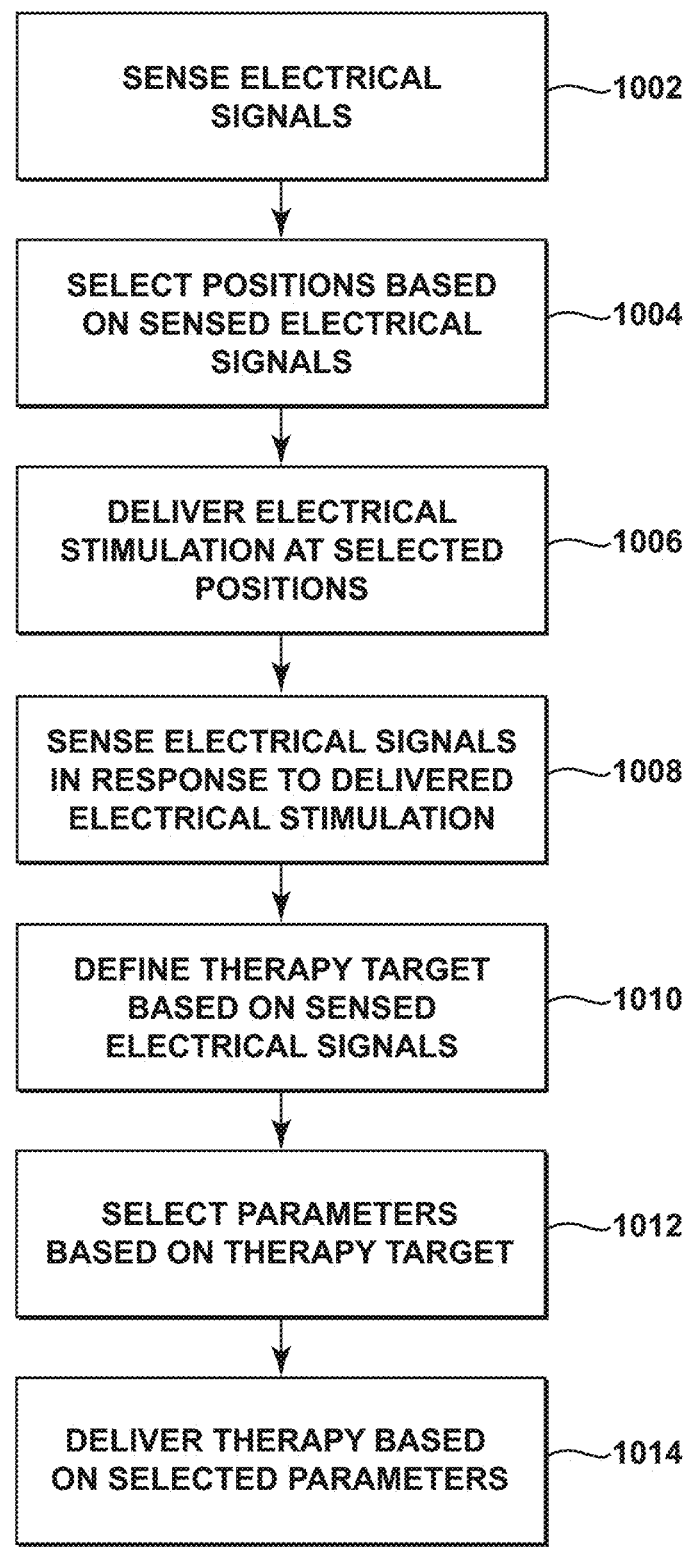
FIG. 10 is a flow diagram of an example technique for defining a therapy target, selecting therapy parameters based on the therapy target definition, and delivering therapy to a brain of a patient based on the selected parameters.

FIG. 10 is a flow diagram of another example technique for defining a therapy target, selecting therapy parameters based on the therapy target definition, and delivering therapy to brain 106 of patient 104 based on the selected parameters.

Electrical signals may be sensed at different positions when electrical stimulation is not delivered (1002). For example, sensing circuitry 206 may sense electrical signals at the different positions when electrical stimulation is not delivered. For example, as described with reference to FIGS. 4A-9, electrodes 118 corresponding to different axial positions along the length of a lead such as lead 114, and/or different circumferential positions about the circumference of the lead may be used to sense electrical signals when electrical stimulation is not delivered at those positions. For example, local field potentials may be sensed at each of those positions.

In some examples, a plurality of different positions for delivery of the electrical stimulation may be selected based on the electrical signals sensed at the different positions when electrical stimulation is not delivered (1004). For example, controller 202 and/or controller 302 may select a plurality of different positions for delivery of the electrical stimulation based on electrical signals sensed at the different positions when electrical stimulation is not delivered. For example, as described with reference to FIGS. 4A-10, local field potentials over a predetermined threshold amount may be indicative of a position of interest such that controller 202 and/or controller 302 may select positions with local field potentials over the predetermined threshold amount for electrical stimulation and, thus, further analysis. In other examples, the one or more positions of interest may be selected using a signal other than, or in addition to, a local field potential signal, such as a microelectrode recording. Moreover, the signal characteristic upon which the selection is based may be a characteristic other than, or in addition to, amplitude such as frequency, waveform morphology, power level in a particular frequency band, or any other signal characteristic in the time domain or frequency domain.

Electrical stimulation may be delivered at a plurality of different intensities at each of the selected plurality of different positions within brain 106 of patient 104 via selected combinations of electrodes 108 (1006), as described in further detail with respect to FIG. 9. As previously described, the selected positions for delivering electrical stimulation may be selected based on the sensed local field potentials corresponding to those positions when electrical stimulation is not delivered at those positions. The stimulation at different intensities may be delivered as a progression of stimulation at increasing intensities until a predetermined level of suppression of a sensed beta band signal is sensed or until the beta band signal is maximally suppressed. As stated above, some other signal characteristic instead of or in addition to a beta band signal that is responsive to stimulation may be monitored to determine when that signal characteristic is optimally affected in some predetermined manner by the different stimulation intensities. A signal characteristic may be optimally affected, for instance, when it decreases to some minimum, decreases below some threshold or disappears entirely. In other examples, a signal characteristic may be optimally affected when it increases to some maximum or increases above some threshold. In other cases, the signal characteristic may be considered to be optimally affected when it changes in some other predetermined manner.

Electrical signals may be sensed at each of the different positions within brain 106 of patient 104 in response to the electrical stimulation delivered at each of the different intensities (1008), as described in further detail with respect to FIG. 9.

A therapy target may be defined based on the sensed electrical signals to provide a therapy target definition (1010), as described in further detail with respect to FIG. 9. For example, controller 202 and/or controller 302 may define a therapy target based on the sensed electrical signals. In some examples, definition of the therapy target may be further based on the electrical signals sensed when electrical stimulation is not delivered. For example, sensing local field potentials to determine positions, and determining the responsiveness of the beta band signals to electrical stimulation for each position, may be used to define a therapy target that is indicative of a spatial definition of a source, such as source 108. For example, a position that is associated with a large local field potential and a large suppressive stimulation intensity may indicate a portion of source 108 adjacent to the position that is substantially large. The local field potentials sensed when electrical stimulation is not delivered and the responsiveness of the beta band signals to electrical stimulation for each position may be used to develop a mapping of the spatial extent of source 108 that may be used for selection of therapy parameters to treat or monitor source 108 and/or monitor movement of lead 114 and/or electrodes with respect to source 108.

In some examples, the local field potentials sensed when electrical stimulation is not delivered and/or the responsiveness of the beta band signals to electrical stimulation for one or more positions may be used to define a therapy target, the definition of which includes information that may be used to derive a mapping of the spatial extent of the source 108 but may not itself include the mapping. For example, the therapy target definition may include, for one or more positions, the measurements of the local field potentials sensed when electrical stimulation is not delivered and/or the responsiveness of the beta band signals to electrical stimulation.

In some examples, the therapy target definition may include both a mapping of the spatial extent of source 108 and/or other information that may be useful for selecting therapy parameters including, for example, the responsiveness of the beta band signals to electrical stimulation at one more positions.

One or more parameters of therapy to be delivered to a brain of a patient may be selected based on the therapy target definition (1012), as also discussed with reference to FIG. 9.

Therapy parameters may be selected based on a mapping of the spatial extent of source 108 and/or based on other information in the definition of the therapy target. For example, parameters for forming a lesion and/or for monitoring source 108 and/or the position of lead 114 and/or electrodes with respect to source may be selected based on a mapping of the spatial extent of source 108. As another example, parameters for delivering electrical stimulation for treatment of source 108 may be selected based on the responsiveness of the beta band signals to electrical stimulation. For example, selecting the parameters may include selecting intensities for electrical stimulation that are equivalent to or some other function of the intensities determined to be suppressive.

Delivery of therapy to brain 106 of patient 104 may be controlled based on the selected therapy parameters (1014), as discussed with reference to FIG. 9. For example, controller 202 and/or controller 302 may control delivery of therapy to brain 106 of patient 104 based on the therapy target definition. A defined target that corresponds to a spatial extent of a source, such as source 108, may be used to deliver treatment using electrical stimulation for suppression of symptoms, including for forming a lesion, to monitor changes to source 108 and/or movement of lead 114 with respect to source 108, and/or for any other suitable treatment or use according to particular needs.

Any suitable modifications to the described techniques may be made according to particular needs. Although the techniques have been described to include sensing of beta band signals, the technique may include, alternatively or in addition, sensing of gamma band signals. For example, changes in sensed gamma band signals in response to delivery of electrical stimulation may also be used to define a therapy target corresponding to a spatial extent of a source, such as source 108. Sensing of other electrical signals that may change in response to delivery of electrical stimulation may also be used for defining the therapy target according to particular needs. Additionally, delivery of electrical stimulation and sensing of electrical signals in response to the delivery of electrical stimulation may be performed for one or more positions before being performed at other positions. In some examples, these steps may be performed simultaneously for all positions. In some examples, different electrodes or groups of electrodes may be used for delivery of electrical stimulation and sensing of electrical signals. In other examples, the same electrodes and/or groups of electrodes may be used for delivery of electrical stimulation and sensing of electrical signals. In some examples, the same or different electrodes or groups of electrodes may be used for sensing of electrical signals before delivery of electrical stimulation and for sensing of electrical signals in response to the delivery of electrical stimulation.

Additionally, multiple steps described as being performed by controller 202 and/or controller 302 may be performed by either controller 202 or controller 302, both controller 202 and controller 302, and/or any other suitable device or component according to particular needs.

In some examples, the positions for sensing local field potentials and/or delivering electrical stimulation and sensing electrical signals in response to the delivered electrical stimulation, may be adjacent to one other on a lead, whether axially adjacent or circumferentially adjacent. In other examples, the positions may not be adjacent to one another.

The techniques described in this disclosure, including those attributed to programmer 120, IMD 110, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "controller," "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by controller 202 of IMD 110 and/or controller 302 of programmer 120, any one or more parts of the techniques described herein may be implemented by a controller of one of IMD 110, programmer 120, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various embodiments of have been described. These and other embodiments are within the scope of the following claims.

What is claimed is:

1. A method for delivering electrical stimulation therapy to a patient, the method comprising:
sensing, by sensing circuitry and via one or more of a plurality of electrodes of an implantable medical device (IMD), a first plurality of electrical signals at each of a plurality of different positions within a brain of the patient when electrical stimulation is not delivered at each of the positions;
selecting, based on the first plurality of electrical signals sensed at each of the plurality of different positions within the brain of the patient when electrical stimulation is not delivered at each of the positions, a subset of the plurality of different positions within the brain of the patient;
delivering, by electrical stimulation circuitry of the IMD, electrical stimulation at each of a plurality of different intensities at each position of the subset of the plurality of different positions via one or more of the plurality of electrodes;
sensing, by the sensing circuitry and via one or more of the plurality of electrodes, a second plurality of electrical signals at each position of the subset of the plurality of different positions in response to the electrical stimulation delivered at each position of the subset of the plurality of different positions at the plurality of different intensities, wherein the second plurality of electrical signals spatially define a source of the second plurality of electrical signals within the brain of the patient;

selecting, by processing circuitry, one or more parameters of electrical stimulation therapy to be delivered to the brain of the patient, wherein the parameters are selected based on:
- the first plurality of electrical signals sensed at each of the plurality of different positions within the brain of the patient when electrical stimulation is not delivered at each of the positions; and
- the second plurality of electrical signals sensed at each position of the subset of the plurality of different positions within the brain of the patient in response to the electrical stimulation delivered at each position of the subset of the plurality of different positions at the plurality of different intensities, wherein the second plurality of electrical signals spatially define the source of the second plurality of electrical signals within the brain of the patient; and controlling, by the processing circuitry, the electrical stimulation circuitry to deliver the electrical stimulation therapy to the brain of the patient based on the selected one or more parameters and via one or more electrodes of the plurality of electrodes.

2. The method of claim 1,
wherein the electrical stimulation comprises first electrical stimulation,
wherein selecting the one or more parameters comprises:
- selecting at least some of the different positions based on the sensed first and second plurality of electrical signals and the first electrical stimulation; and
- selecting intensities for each of respective positions of the at least some of the different positions based on the sensed first and second plurality of electrical signals and the first electrical stimulation, and wherein controlling the electrical stimulation circuitry to deliver the electrical stimulation therapy to the brain of the patient based on the selected one or more parameters comprises controlling the electrical stimulation circuitry to deliver second electrical stimulation to the brain at each position of the at least some of the different positions at the intensities selected for each of the respective positions of the at least some of the different positions.

3. The method of claim 2, wherein
delivering the second electrical stimulation to the brain at each position of the at least some of the different positions comprises delivering the second electrical stimulation via one or more electrodes of the plurality of electrodes implanted proximate to the respective positions of the at least some of the different positions.

4. The method of claim 3, wherein at least some of the plurality of electrodes are carried by a lead implanted in the patient.

5. The method of claim 4,
wherein sensing the first plurality of electrical signals at each of the plurality of different positions comprises sensing the first plurality of electrical signals at each of the plurality of different positions via one or more of the plurality of electrodes implanted proximate to the respective positions of the different positions, and
wherein sensing the second plurality of electrical signals at each position of the subset of the plurality of different positions comprises sensing the second plurality of electrical signals at each position of the subset of the different positions via one or more electrodes of a subset of the plurality of electrodes implanted proximate to the respective positions of the subset of the different positions.

6. The method of claim 2, further comprising selecting the intensities for each of the respective positions of the at least some of the different positions based on intensities of the first electrical stimulation delivered at the subset of the plurality of different positions.

7. The method of claim 2, wherein the second plurality of electrical signals comprise beta band signals, and selecting intensities for each of the at least some of the different positions comprises selecting intensities at which the first electrical stimulation suppresses the sensed beta band signals by a greater amount relative to other intensities that are not selected.

8. The method of claim 2, wherein the selected at least some of the different positions comprise all of the subset of the plurality of different positions to which the first electrical stimulation was delivered.

9. The method of claim 2,
wherein sensing the first plurality of electrical signals at each of the plurality of different positions comprises sensing the first plurality of electrical signals at each of the plurality of different positions via one or more of the plurality of electrodes implanted proximate to the respective positions of the different positions,
wherein sensing the second plurality of electrical signals at each position of the subset of the plurality of different positions comprises sensing the second plurality of electrical signals at each position of the subset of the plurality of different positions via one or more electrodes of one or more electrodes of a subset of the plurality of electrodes implanted proximate to the respective positions of the subset of the plurality of the different positions, and
wherein the subset of the plurality of different positions comprises combinations of a plurality of axial positions along a length of the lead and a plurality of circumferential positions about a circumference of the lead.

10. The method of claim 2,
wherein sensing the first plurality of electrical signals at each of the plurality of different positions comprises sensing the first plurality of electrical signals at each of the plurality of different positions via one or more of the plurality of electrodes implanted proximate to the respective positions of the different positions,
wherein sensing the second plurality of electrical signals at each position of the subset of the plurality of different positions comprises sensing the second plurality of electrical signals at each position of the subset of the plurality of different positions via one or more electrodes of a subset of the plurality of electrodes implanted proximate to the respective positions of the at least a subset of the plurality of the different positions, and
wherein the subset of the plurality of different positions comprises at least one of a plurality of axial positions along a length of the lead or a plurality of circumferential positions about a circumference of the lead.

11. The method of claim 2, wherein
controlling the electrical stimulation circuitry to deliver the second electrical stimulation to the brain of the patient based on the selected one or more parameters comprises controlling the electrical stimulation circuitry to deliver electrical energy to the brain at each position of the at least some of the plurality of different positions at intensities sufficient to form one or more lesions in the brain.

12. The method of claim 1, further comprising determining, by the processing circuitry, a sequence for delivery of the electrical stimulation therapy based on the first plurality of electrical signals.

13. The method of claim 12, wherein determining the sequence for delivery of the electrical stimulation therapy based on the first plurality of electrical signals comprises selecting a starting position of the plurality of different positions corresponding to a sensed electrical signal of the first plurality of sensed electrical signals having a measurement with a highest value of measurements for each electrical signal of the first plurality of electrical signals.

14. The method of claim 1,
wherein sensing the first plurality of electrical signals at each of the plurality of different positions comprises sensing the first plurality of electrical signals at each of the plurality of different positions via one or more of the plurality of electrodes implanted proximate to the respective positions of the different positions, and
wherein sensing the second plurality of electrical signals at each position of the subset of the plurality of different positions comprises sensing the second plurality of electrical signals at each position of the subset of the different positions via one or more electrodes of a subset of the plurality of electrodes implanted proximate to the respective positions of the subset of the different positions.

15. The method of claim 1, wherein selecting the parameters comprises selecting the parameters based on the sensed second plurality of electrical signals and intensities of the delivered electrical stimulation in response to which the second plurality of electrical signals were sensed, wherein the intensities and the sensed second plurality of electrical signals spatially define the source of the second plurality of electrical signals within the brain of the patient.

16. The method of claim 1, wherein the different positions are adjacent to one another.

17. The method of claim 1, wherein at least some of the plurality of electrodes of the IMD are implanted within the brain of the patient.

18. The method of claim 1, wherein an external programmer comprises the processing circuitry.

19. The method of claim 1, wherein the IMD comprises the processing circuitry.

20. The method of claim 1, wherein the one or more electrodes with which the sensing circuitry senses the first plurality of electrical signals, the one or more electrodes with which the electrical stimulation circuitry delivers the electrical stimulation at each of the plurality of different intensities at each position of the subset of the plurality of different positions, and the one or more electrodes with which the sensing circuitry senses the second plurality of electrical signals are different electrodes of the plurality of electrodes.

21. The method of claim 1, wherein the one or more electrodes with which the sensing circuitry senses the first plurality of electrical signals, the one or more electrodes with which the electrical stimulation circuitry delivers the electrical stimulation at each of the plurality of different intensities at each position of the subset of the plurality of different positions, and the one or more electrodes with which the sensing circuitry senses the second plurality of electrical signals include at least one common electrode of the plurality of electrodes.

22. A system for delivering electrical stimulation therapy, the system comprising:
a plurality of electrodes of an implantable medical device (IMD);
electrical stimulation circuitry of the IMD;
sensing circuitry configured to sense, via one or more of the plurality of electrodes, a first plurality of electrical signals at each of a plurality of different positions within a brain of the patient when electrical stimulation is not delivered at each of the positions;
a controller comprising processing circuitry configured to:
select, based on the first plurality of electrical signals sensed at each of the plurality of different positions within the brain of the patient when electrical stimulation is not delivered at each of the positions, a subset of the plurality of different positions within the brain of the patient; and
control the electrical stimulation circuitry to deliver electrical stimulation at each of a plurality of different intensities at each position of the subset of the plurality of different positions via one or more of the plurality of electrodes;
wherein the sensing circuitry is further configured to sense, via one or more of the plurality of electrodes, a second plurality of electrical signals at each position of the subset of the plurality of different positions in response to the electrical stimulation delivered at each position of the subset of the plurality of different positions at the plurality of different intensities, wherein the second plurality of electrical signals spatially define a source of the second plurality of electrical signals within the brain of the patient, and
wherein the processing circuitry is further configured to:
select one or more parameters of electrical stimulation therapy to be delivered to the brain of the patient, wherein the parameters are selected based on:
the first plurality of electrical signals sensed at each of the plurality of different positions within the brain of the patient when electrical stimulation is not delivered at each of the positions; and
the second plurality of electrical signals sensed at each position of the subset of the different positions within the brain of the patient in response to the electrical stimulation delivered at each position of the subset of the plurality of different positions at the plurality of different intensities, wherein the second plurality of electrical signals spatially define the source of the second plurality of electrical signals within the brain of the patient; and
control the electrical stimulation circuitry to deliver the electrical stimulation therapy to the brain of the patient based on the selected one or more parameters and via one or more electrodes of the plurality of electrodes.

23. The system of claim 22,
wherein the electrical stimulation comprises first electrical stimulation,
wherein the controller is further configured to select the one or more parameters by:
selecting at least some of the different positions based on the sensed first and second plurality of electrical signals and the first electrical stimulation; and selecting intensities for each of respective positions of the at least some of the different positions based on the sensed first and second plurality of electrical signals and the first electrical stimulation, and wherein the controller is further configured to control the electrical stimulation circuitry to deliver the electrical stimulation therapy to the brain of the patient based on the selected one or more parameters by controlling the electrical stimulation circuitry to deliver second electrical stimulation to the brain at each position of the at least some of the different positions at the intensities selected for each of the respective positions of the at least some of the different positions.

24. The system of claim 23, wherein the controller is further configured to control the electrical stimulation circuitry to deliver the second electrical stimulation to the brain at each position of the at least some of the different positions by controlling the electrical stimulation circuitry to deliver the second electrical stimulation via one or more electrodes of the plurality of electrodes implanted proximate to the respective positions of the at least some of the different positions.

25. The system of claim 24, wherein at least some of the plurality of electrodes are carried by a lead implantable in the patient.

26. The system of claim 25, wherein the sensing circuitry is further configured to sense the first plurality of electrical signals at each of the plurality of different positions by sensing the first plurality of electrical signals at each of the plurality of different positions via one or more of the plurality of electrodes implanted proximate to the respective positions of the different positions, and wherein the sensing circuitry is further configured to sense the second plurality of electrical signals by sensing the second plurality of electrical signals at each position of the subset of the different positions via one or more electrodes of a subset of the plurality of electrodes implanted proximate to the respective positions of the subset of the different positions.

27. The system of claim 23, wherein the controller is further configured to select the intensities for each of the respective positions of the at least some of the different positions based on intensities of the first electrical stimulation delivered at the subset of the different positions.

28. The system of claim 23, wherein the second plurality of electrical signals comprise beta band signals, and the controller is further configured to select intensities for each of the at least some of the different positions by selecting intensities at which the first electrical stimulation suppresses the sensed beta band signals by a greater amount relative to other intensities that are not selected.

29. The system of claim 23, wherein the selected at least some of the different positions comprise all of the subset of the plurality of different positions to which the first electrical stimulation was delivered.

30. The system of claim 23, wherein the sensing circuitry is further configured to sense the first plurality of electrical signals at each of the plurality of different positions by sensing the first plurality of electrical signals at each of the plurality of different positions via one or more of the plurality of electrodes implanted proximate to the respective positions of the different positions, wherein the sensing circuitry is further configured to sense the second plurality of electrical signals by sensing the second plurality of electrical signals at each position of the subset of the plurality of different positions via one or more electrodes of a subset of the plurality of electrodes implantable proximate to the respective positions of the subset of the plurality of different positions, and wherein the subset of the plurality of different positions comprises combinations of a plurality of axial positions along a length of the lead and a plurality of circumferential positions about a circumference of the lead.

31. The system of claim 23, wherein the sensing circuitry is further configured to sense the first plurality of electrical signals at each of the plurality of different positions by sensing the first plurality of electrical signals at each of the plurality of different positions via one or more of the plurality of electrodes implanted proximate to the respective positions of the different positions, wherein the sensing circuitry is further configured to sense the second plurality of electrical signals by sensing the second plurality of electrical signals at each position of the subset of the plurality of different positions via a subset of the plurality of electrodes implantable proximate to the respective positions of the subset of the different positions, and wherein the subset of the plurality of different positions comprises at least one of a plurality of axial positions along a length of the lead or a plurality of circumferential positions about a circumference of the lead.

32. The system of claim 23, wherein the controller is further configured to control the electrical stimulation circuitry to deliver the second electrical stimulation to the brain of the patient based on the selected one or more parameters by delivering electrical energy to the brain at each position of the at least some of the plurality of different positions at intensities sufficient to form one or more lesions in the brain.

33. The system of claim 22, wherein the controller is further configured to determine a sequence for delivery of the electrical stimulation based on the first plurality of electrical signals.

34. The system of claim 33, wherein the controller is further configured to determine the sequence for delivery of the electrical stimulation based on the first plurality of electrical signals by selecting a starting position of the plurality of different positions corresponding to a sensed electrical signal of the first plurality of electrical signals having a measurement with a highest value of measurements for each electrical signal of the first plurality of electrical signals.

35. The system of claim 22, wherein the sensing circuitry is further configured to sense the first plurality of electrical signals at each of the plurality of different positions by sensing the first plurality of electrical signals at each of the plurality of different positions via one or more of the plurality of electrodes implanted proximate to the respective positions of the different positions, and wherein the sensing circuitry is further configured to sense the second plurality of electrical signals by sensing the second plurality of electrical signals at each position of the subset of the different positions via one or more electrodes of a subset of the plurality of electrodes implantable proximate to the respective positions of the subset of the different positions.

36. The system of claim 22, wherein the controller is further configured to select the parameters based on the sensed first and second plurality of electrical signals and the delivered electrical stimulation by selecting the parameters based on the sensed second plurality of electrical signals and intensities of the delivered electrical stimulation in response to which the second plurality of electrical signals were sensed, wherein the intensities and the sensed second plurality of electrical signals spatially define the source of the second plurality of electrical signals within the brain of the patient.

37. The system of claim 22, wherein the different positions are adjacent to one another.

38. A system for delivering electrical stimulation therapy to a patient, the system comprising:
- means for sensing, via one or more of a plurality of electrodes of an implantable medical device (IMD), a first plurality of electrical signals at each of a plurality of different positions within a brain of the patient when electrical stimulation is not delivered at each of the positions;
- means for selecting, based on the first plurality of electrical signals sensed at each of the plurality of different positions within the brain of the patient when electrical stimulation is not delivered at each of the positions, a subset of the plurality of different positions within the brain of the patient;
- means for delivering electrical stimulation at each of a plurality of different intensities at each position of the subset of the plurality of different positions via one or more of the plurality of electrodes;
- means for sensing, via one or more of the plurality of electrodes, a second plurality of electrical signals at each position of the subset of the plurality of different positions in response to the electrical stimulation delivered at each position of the subset of the plurality of different positions at the plurality of different intensities, wherein the second plurality of electrical signals spatially define a source of the second plurality of electrical signals within the brain of the patient;
- means for selecting one or more parameters of electrical stimulation therapy to be delivered to the brain of the patient, wherein the parameters are selected based on:
  - the first plurality of electrical signals sensed at the plurality of different positions within the brain of the patient when electrical stimulation is not delivered at each of the positions; and
  - the second plurality of electrical signals sensed at each of the at least a subset of different positions within the brain of the patient in response to electrical stimulation delivered at each of the at least a subset of the plurality of different positions;
- means for delivering the electrical stimulation therapy to the brain of the patient, wherein the second plurality of electrical signals spatially define the source of the second plurality of electrical signals within the brain of the patient; and
- means for controlling the means for delivering the electrical stimulation therapy to deliver the electrical stimulation therapy to the brain of the patient based on the selected one or more parameters and via one or more electrodes of the plurality of electrodes.

39. The system of claim 38, further comprising means for determining a sequence for delivery of the electrical stimulation therapy based on the first plurality of electrical signals.

40. The system of claim 39, further comprising means for determining the sequence for delivery of the electrical stimulation therapy based on the first plurality of electrical signals by selecting a starting position of the plurality of different positions corresponding to a sensed electrical signal of the first plurality of electrical signals having a measurement with a highest value of measurements for each electrical signal of the first plurality of electrical signals.

41. The system of claim 38, wherein the electrical stimulation comprises first electrical stimulation, and
wherein the means for selecting the one or more parameters comprises:
- means for selecting at least some of the different positions based on the sensed first and second plurality of electrical signals and the first electrical stimulation; and
- means for selecting intensities for each of respective positions of the at least some of the different positions based on the sensed first and second plurality of electrical signals and the delivered electrical stimulation, and
wherein the means for controlling the means for delivering electrical stimulation to deliver the therapy to the brain of the patient based on the selected one or more parameters is configured to control the means for delivering electrical stimulation to deliver second electrical stimulation to the brain at the at least some of the different positions at the intensities selected for each of the respective positions of the at least some of the different positions.

42. The system of claim 41, further comprising means for selecting the intensities for each of the respective positions of the at least some of the different positions based on intensities of the electrical stimulation delivered at the different positions.

* * * * *